(12) United States Patent
Kopelman et al.

(10) Patent No.: US 10,406,753 B2
(45) Date of Patent: *Sep. 10, 2019

(54) SYSTEM AND METHOD FOR MANUFACTURING A DENTAL PROSTHESIS AND A DENTAL PROSTHESIS MANUFACTURED THEREBY

(71) Applicant: Align Technology, Inc., San Jose, CA (US)

(72) Inventors: Avi Kopelman, Palo Alto, CA (US); Eldad Taub, Reut (IL)

(73) Assignee: Align Technology, Inc., San Jose, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/041,532

(22) Filed: Jul. 20, 2018

(65) Prior Publication Data

US 2019/0054698 A1    Feb. 21, 2019

Related U.S. Application Data

(63) Continuation of application No. 14/533,033, filed on Nov. 4, 2014, now Pat. No. 10,059,059, which is a
(Continued)

(51) Int. Cl.
*B29C 64/386* (2017.01)
*A61C 5/77* (2017.01)
(Continued)

(52) U.S. Cl.
CPC .............. *B29C 64/386* (2017.08); *A61C 5/77* (2017.02); *A61C 13/00* (2013.01);
(Continued)

(58) Field of Classification Search
CPC ... B29C 64/386; A61C 13/0004; A61C 13/09; A61C 13/77; A61C 13/00; G05B 19/4097; G05B 2219/45167; G06F 17/50
See application file for complete search history.

(56) References Cited

U.S. PATENT DOCUMENTS 2,467,432 A    4/1949    Kesling et al.
3,407,500 A    10/1968   Kesling et al.
(Continued)

FOREIGN PATENT DOCUMENTS

AU    3031677 A    5/1979
AU    517102 B2    7/1981
(Continued)

OTHER PUBLICATIONS

AADR. American Association for Dental Research, Summary of Activities, Mar. 20-23, 1980, Los Angeles, CA, p. 195.
(Continued)

*Primary Examiner* — Nathan L Laughlin
(74) *Attorney, Agent, or Firm* — Wilson Sonsini Goodrich & Rosati

(57) ABSTRACT

A dental prosthesis is made by externally machining successive layers of wax, each of which is formed on a previous prosthesis layer and/or on a coping. Each wax layer is used to form a mold in situ over the previous prosthesis layer/coping, and the appropriate prosthesis material is cast or otherwise molded to conform to the wax layer by the mold.

19 Claims, 13 Drawing Sheets

Related U.S. Application Data continuation of application No. 12/659,385, filed on Mar. 8, 2010, now Pat. No. 8,909,363, which is a continuation of application No. 11/783,149, filed on Apr. 6, 2007, now Pat. No. 7,689,310, which is a continuation of application No. 11/290,449, filed on Dec. 1, 2005, now Pat. No. 7,236,842.

(60) Provisional application No. 60/632,350, filed on Dec. 2, 2004.

(51) Int. Cl.
*A61C 13/00* (2006.01)
*A61C 13/20* (2006.01)
*A61C 13/09* (2006.01)
*G05B 19/4097* (2006.01)
*G06F 17/50* (2006.01)
*G16H 20/40* (2018.01)

(52) U.S. Cl.
CPC .......... *A61C 13/0004* (2013.01); *A61C 13/09* (2013.01); *A61C 13/20* (2013.01); *G05B 19/4097* (2013.01); *G06F 17/50* (2013.01); *G05B 2219/45167* (2013.01); *G16H 20/40* (2018.01)

(56) References Cited

U.S. PATENT DOCUMENTS

| | | |
|---|---|---|
| 3,600,808 A | 8/1971 | Reeve et al. |
| 3,660,900 A | 5/1972 | Andrews et al. |
| 3,683,502 A | 8/1972 | Wallshein et al. |
| 3,738,005 A | 6/1973 | Cohen et al. |
| 3,860,803 A | 1/1975 | Levine et al. |
| 3,916,526 A | 11/1975 | Schudy et al. |
| 3,922,786 A | 12/1975 | Lavin et al. |
| 3,950,851 A | 4/1976 | Bergersen et al. |
| 3,983,628 A | 10/1976 | Acevedo et al. |
| 4,014,096 A | 3/1977 | Dellinger et al. |
| 4,195,046 A | 3/1980 | Kesling et al. |
| 4,253,828 A | 3/1981 | Coles et al. |
| 4,324,546 A | 4/1982 | Heitlinger et al. |
| 4,324,547 A | 4/1982 | Arcan et al. |
| 4,348,178 A | 9/1982 | Kurz |
| 4,411,626 A | 10/1983 | Becker et al. |
| 4,478,580 A | 10/1984 | Barrut et al. |
| 4,500,294 A | 2/1985 | Lewis et al. |
| 4,504,225 A | 3/1985 | Yoshii |
| 4,505,673 A | 3/1985 | Yoshii et al. |
| 4,526,540 A | 7/1985 | Dellinger et al. |
| 4,575,330 A | 3/1986 | Hull et al. |
| 4,575,805 A | 3/1986 | Moermann et al. |
| 4,591,341 A | 5/1986 | Andrews et al. |
| 4,609,349 A | 9/1986 | Cain et al. |
| 4,611,288 A | 9/1986 | Duret et al. |
| 4,656,860 A | 4/1987 | Orthuber et al. |
| 4,663,720 A | 5/1987 | Duret et al. |
| 4,664,626 A | 5/1987 | Kesling et al. |
| 4,676,747 A | 6/1987 | Kesling et al. |
| 4,742,464 A | 5/1988 | Duret et al. |
| 4,755,139 A | 7/1988 | Abbatte et al. |
| 4,763,791 A | 8/1988 | Halverson et al. |
| 4,793,803 A | 12/1988 | Martz et al. |
| 4,798,534 A | 1/1989 | Breads et al. |
| 4,836,778 A | 6/1989 | Baumrind et al. |
| 4,837,732 A | 6/1989 | Brandestini et al. |
| 4,850,864 A | 7/1989 | Diamond et al. |
| 4,850,865 A | 7/1989 | Napolitano et al. |
| 4,856,991 A | 8/1989 | Breads et al. |
| 4,877,398 A | 10/1989 | Kesling et al. |
| 4,880,380 A | 11/1989 | Martz et al. |
| 4,889,238 A | 12/1989 | Batchelor et al. |
| 4,890,608 A | 1/1990 | Steer et al. |
| 4,935,635 A | 6/1990 | O'Harra et al. |
| 4,936,862 A | 6/1990 | Walker et al. |
| 4,937,928 A | 7/1990 | Van et al. |
| 4,941,826 A | 7/1990 | Loran et al. |
| 4,964,770 A | 10/1990 | Steinbichler et al. |
| 4,975,052 A | 12/1990 | Spencer et al. |
| 4,983,334 A | 1/1991 | Adell et al. |
| 5,011,405 A | 4/1991 | Lemchen et al. |
| 5,017,133 A | 5/1991 | Miura et al. |
| 5,027,281 A | 6/1991 | Rekow et al. |
| 5,035,613 A | 7/1991 | Breads et al. |
| 5,055,039 A | 10/1991 | Abbatte et al. |
| 5,059,118 A | 10/1991 | Breads et al. |
| 5,100,316 A | 3/1992 | Wildman et al. |
| 5,121,333 A | 6/1992 | Riley et al. |
| 5,125,832 A | 6/1992 | Kesling |
| 5,128,870 A | 7/1992 | Erdman et al. |
| 5,130,064 A | 7/1992 | Smalley et al. |
| 5,131,843 A | 7/1992 | Hilgers et al. |
| 5,131,844 A | 7/1992 | Marinaccio et al. |
| 5,139,419 A | 8/1992 | Andreiko et al. |
| 5,145,364 A | 9/1992 | Martz et al. |
| 5,176,517 A | 1/1993 | Truax et al. |
| 5,184,306 A | 2/1993 | Erdman et al. |
| 5,186,623 A | 2/1993 | Breads et al. |
| 5,257,203 A | 10/1993 | Riley et al. |
| 5,266,030 A | 11/1993 | Van Der Zel |
| 5,273,429 A | 12/1993 | Rekow et al. |
| 5,278,756 A | 1/1994 | Lemchen et al. |
| 5,328,362 A | 7/1994 | Watson et al. |
| 5,338,198 A | 8/1994 | Wu et al. |
| 5,340,309 A | 8/1994 | Robertson et al. |
| 5,342,201 A | 8/1994 | Oden |
| 5,342,202 A | 8/1994 | Deshayes et al. |
| 5,368,478 A | 11/1994 | Andreiko et al. |
| 5,378,154 A | 1/1995 | Van Der Zel |
| 5,382,164 A | 1/1995 | Stern et al. |
| 5,395,238 A | 3/1995 | Andreiko et al. |
| 5,431,562 A | 7/1995 | Andreiko et al. |
| 5,440,326 A | 8/1995 | Quinn et al. |
| 5,440,496 A | 8/1995 | Andersson et al. |
| 5,447,432 A | 9/1995 | Andreiko et al. |
| 5,452,219 A | 9/1995 | Dehoff et al. |
| 5,454,717 A | 10/1995 | Andreiko et al. |
| 5,456,600 A | 10/1995 | Andreiko et al. |
| 5,474,448 A | 12/1995 | Andreiko et al. |
| RE35,169 E | 3/1996 | Lemchen et al. |
| 5,518,397 A | 5/1996 | Andreiko et al. |
| 5,528,735 A | 6/1996 | Strasnick et al. |
| 5,533,895 A | 7/1996 | Andreiko et al. |
| 5,542,842 A | 8/1996 | Andreiko et al. |
| 5,549,476 A | 8/1996 | Stern et al. |
| 5,562,448 A | 10/1996 | Mushabac et al. |
| 5,587,912 A | 12/1996 | Andersson et al. |
| 5,605,459 A | 2/1997 | Kuroda et al. |
| 5,607,305 A | 3/1997 | Andersson et al. |
| 5,614,075 A | 3/1997 | Andre, Sr. et al. |
| 5,621,648 A | 4/1997 | Crump et al. |
| 5,645,420 A | 7/1997 | Bergersen et al. |
| 5,645,421 A | 7/1997 | Slootsky et al. |
| 5,652,709 A | 7/1997 | Andersson et al. |
| 5,655,653 A | 8/1997 | Chester et al. |
| 5,683,243 A | 11/1997 | Andreiko et al. |
| 5,692,894 A | 12/1997 | Schwartz et al. |
| 5,725,376 A | 3/1998 | Poirier et al. |
| 5,725,378 A | 3/1998 | Wang et al. |
| 5,733,126 A | 3/1998 | Andersson et al. |
| 5,740,267 A | 4/1998 | Echerer et al. |
| 5,742,700 A | 4/1998 | Yoon et al. |
| 5,799,100 A | 8/1998 | Clarke et al. |
| 5,800,174 A | 9/1998 | Andersson et al. |
| 5,823,778 A | 10/1998 | Schmitt et al. |
| 5,848,115 A | 12/1998 | Little et al. |
| 5,857,853 A | 1/1999 | Van et al. |
| 5,866,058 A | 2/1999 | Batchelder et al. |
| 5,879,158 A | 3/1999 | Doyle et al. |
| 5,880,961 A | 3/1999 | Crump et al. |
| 5,880,962 A | 3/1999 | Andersson et al. |
| 5,934,288 A | 8/1999 | Avila et al. |
| 5,938,446 A | 8/1999 | Andersson et al. |

(56) References Cited

U.S. PATENT DOCUMENTS

| | | | |
|---|---|---|---|
| 5,957,686 A | 9/1999 | Anthony et al. |
| 5,964,587 A | 10/1999 | Sato et al. |
| 5,971,754 A | 10/1999 | Sondhi et al. |
| 5,975,893 A | 11/1999 | Chishti et al. |
| 6,015,289 A | 1/2000 | Andreiko et al. |
| 6,044,309 A | 3/2000 | Honda et al. |
| 6,049,743 A | 4/2000 | Baba et al. |
| 6,062,861 A | 5/2000 | Andersson |
| 6,068,482 A | 5/2000 | Snow et al. |
| 6,099,314 A | 8/2000 | Kopelman et al. |
| 6,123,544 A | 9/2000 | Cleary et al. |
| 6,126,732 A | 10/2000 | Hofmann et al. |
| 6,152,731 A | 11/2000 | Jordan et al. |
| 6,174,158 B1 | 1/2001 | Seres, Jr. et al. |
| 6,174,168 B1 | 1/2001 | Dehoff et al. |
| 6,183,248 B1 | 2/2001 | Chishti et al. |
| 6,190,165 B1 | 2/2001 | Andreiko et al. |
| 6,217,325 B1 | 4/2001 | Chishti et al. |
| 6,217,334 B1 | 4/2001 | Hultgren et al. |
| 6,244,861 B1 | 6/2001 | Andreiko et al. |
| 6,309,215 B1 | 10/2001 | Phan et al. |
| 6,315,553 B1 | 11/2001 | Sachdeva et al. |
| 6,322,359 B1 | 11/2001 | Jordan et al. |
| 6,334,853 B1 | 1/2002 | Kopelman et al. |
| 6,350,120 B1 | 2/2002 | Sachdeva et al. |
| 6,364,660 B1 | 4/2002 | Durbin et al. |
| 6,382,975 B1 | 5/2002 | Poirier et al. |
| 6,398,548 B1 | 6/2002 | Muhammad et al. |
| 6,402,707 B1 | 6/2002 | Ernst et al. |
| 6,482,298 B1 | 11/2002 | Bhatnagar et al. |
| 6,524,101 B1 | 2/2003 | Phan et al. |
| 6,554,611 B2 | 4/2003 | Shishti et al. |
| 6,572,372 B1 | 6/2003 | Phan et al. |
| 6,594,539 B1 | 7/2003 | Geng |
| 6,629,840 B2 | 10/2003 | Chishti et al. |
| 6,705,863 B2 | 3/2004 | Phan et al. |
| 6,722,880 B2 | 4/2004 | Chishti et al. |
| 6,869,552 B2 | 3/2005 | Glidewell |
| 6,957,118 B2 | 10/2005 | Kopelman et al. |
| 7,236,842 B2 | 6/2007 | Kopelman et al. |
| 7,689,310 B2 | 3/2010 | Kopelman et al. |
| 8,909,363 B2 | 12/2014 | Kopelman et al. |
| 1,005,905 A1 | 8/2018 | Kopelman et al. |
| 2002/0006597 A1 | 1/2002 | Andreiko et al. |
| 2002/0013636 A1 | 1/2002 | Aposbrien |
| 2002/0028418 A1 | 3/2002 | Farag et al. |
| 2002/0058229 A1 | 5/2002 | Sugimoto |
| 2002/0137011 A1 | 9/2002 | Shoher et al. |
| 2003/0009252 A1 | 1/2003 | Pavlovskaia et al. |
| 2003/0139834 A1 | 7/2003 | Nikolskiy et al. |
| 2003/0224311 A1 | 12/2003 | Cronauer et al. |
| 2004/0128010 A1 | 7/2004 | Pavlovskaia et al. |
| 2004/0158342 A1 | 8/2004 | Wolf et al. |
| 2005/0055118 A1 | 3/2005 | Nikolskiy et al. |
| 2005/0080503 A1 | 4/2005 | Kopelman et al. |
| 2005/0147944 A1 | 7/2005 | Karim et al. |
| 2005/0251281 A1 | 11/2005 | O'Brien et al. |
| 2005/0283065 A1 | 12/2005 | Babayoff et al. |
| 2006/0001739 A1 | 1/2006 | Babayoff |
| 2006/0115795 A1 | 6/2006 | Marshall et al. |
| 2010/0167238 A1 | 7/2010 | Kopelman et al. |
| 2011/0049738 A1 | 3/2011 | Sun et al. |

FOREIGN PATENT DOCUMENTS

| | | | |
|---|---|---|---|
| AU | 5598894 A | 6/1994 |
| CA | 1121955 A | 4/1982 |
| DE | 2749802 A1 | 5/1978 |
| DE | 69327661 T2 | 7/2000 |
| EP | 0091876 A1 | 10/1983 |
| EP | 0299490 A2 | 1/1989 |
| EP | 0376873 A2 | 7/1990 |
| EP | 0490848 A2 | 6/1992 |
| EP | 0541500 A1 | 5/1993 |
| EP | 0667753 B1 | 1/2000 |
| EP | 0774933 B1 | 12/2000 |
| EP | 0731673 B1 | 5/2001 |
| ES | 463897 A1 | 1/1980 |
| FR | 2369828 A1 | 6/1978 |
| FR | 2652256 A1 | 3/1991 |
| GB | 1550777 A | 8/1979 |
| JP | S5358191 A | 5/1978 |
| JP | H0428359 A | 1/1992 |
| JP | H08508174 A | 9/1996 |
| WO | WO-9008512 A1 | 8/1990 |
| WO | WO-9104713 A1 | 4/1991 |
| WO | WO-9410935 A1 | 5/1994 |
| WO | WO-9832394 A1 | 7/1998 |
| WO | WO-9844865 A1 | 10/1998 |
| WO | WO-9858596 A1 | 12/1998 |
| WO | WO-0008415 A1 | 2/2000 |
| WO | WO-02071306 A1 | 9/2002 |
| WO | WO-2004008981 A2 | 1/2004 |
| WO | WO-2004087000 A1 | 10/2004 |

OTHER PUBLICATIONS

Alcaniz, et aL, "An Advanced System for the Simulation and Planning of Orthodontic Treatments," Karl Heinz Hohne and Ron Kikinis (eds.), Visualization in Biomedical Computing, 4th Intl. Conf., VBC '96, Hamburg, Germany, Sep. 22-25, 1996, Springer-Verlag, pp. 511-520.

Alexander et al., "The DigiGraph Work Station Part 2 Clinical Management," JCO, pp. 402-407 (Jul. 1990).

Altschuler, "3D Mapping of Maxillo-Facial Prosthesis," AADR Abstract #607, 2 pages total, (1980).

Altschuler et al., "Analysis of 3-D Data for Comparative 3-D Serial Growth Pattern Studies of Oral-Facial Structures," IADR Abstracts, Program and Abstracts of Papers, 57th General Session, IADR Annual Session, Mar. 29, 1979-Apr. 1, 1979, New Orleans Marriot, Journal of Dental Research, vol. 58, Jan. 1979, Special Issue A, p. 221.

Altschuler et al., "Laser Electro-Optic System for Rapid Three-Dimensional (3D) Topographic Mapping of Surfaces," Optical Engineering, 20(6):953-961 (1981).

Altschuler et al., "Measuring Surfaces Space-Coded by a Laser-Projected Dot Matrix," SPIE Imaging Applications for Automated Industrial Inspection and Assembly, vol. 182, p. 187-191 (1979).

Andersson et al., "Clinical Results with Titanium Crowns Fabricated with Machine Duplication and Spark Erosion," Acta. Odontol. Scand., 47:279-286 (1989).

Andrews, The Six Keys to Optimal Occlusion Straight Wire, Chapter 3, pp. 13-24 (1989).

Bartels, et al., An Introduction to Splines for Use in Computer Graphics and Geometric Modeling, Morgan Kaufmann Publishers, pp. 422-425 (1987).

Baumrind, "A System for Craniofacial Mapping Through the Integration of Data from Stereo X-Ray Films and Stereo Photographs," an invited paper submitted to the 1975 American Society of Photogram Symposium on Close-Range Photogram Systems, University of Ill., Aug. 26-30, 1975, pp. 142-166.

Baumrind et al., "A Stereophotogrammetric System for the Detection of Prosthesis Loosening in Total Hip Arthroplasty," NATO Symposium on Applications of Human Biostereometrics, Jul. 9-13, 1978, SPIE, vol. 166, pp. 112-123.

Baumrind et al., "Mapping the Skull in 3-D," reprinted from J. Calif. Dent. Assoc., 48(2), 11 pages total, (1972 Fall Issue).

Baumrind, "Integrated Three-Dimensional Craniofacial Mapping: Background, Principles, and Perspectives," Semin. in Orthod., 7(4):223-232 (Dec. 2001).

Begole et al., "A Computer System for the Analysis of Dental Casts," The Angle Orthod., 51(3):253-259 (Jul. 1981).

Bernard et al., "Computerized Diagnosis in Orthodontics for Epidemiological Studies: A Progress Report," Abstract, J. Dental Res. Special Issue, vol. 67, p. 169, paper presented at International Association for Dental Research 66th General Session, Mar. 9-13, 1988, Montreal, Canada.

(56) References Cited

OTHER PUBLICATIONS

Bhatia et al., "A Computer-Aided Design for Orthognathic Surgery," Br. J. Oral Maxillofac. Surg., 22:237-253 (1984).
Biggerstaff, "Computerized Diagnostic Setups and Simulations," Angle Orthod., 40(1):28-36 (Jan. 1970).
Biggerstaff et al., "Computerized Analysis of Occlusion in the Postcanine Dentition," Am. J. Orthod., 61(3): 245-254 (Mar. 1972).
Biostar Opeation & Training Manual. Great Lakes Orthodontics, Ltd. 199 Fire Tower Drive, Tonawanda, New York. 14150-5890, 20 pages total (1990).
Blu, et al., "Linear interpolation revitalized", IEEE Trans. Image Proc., 13(5):710-719 (May 2004.
Bourke, "Coordinate System Transformation," (Jun. 1996), p. 1, retrieved from the Internet Nov. 5, 2004, URL< http://astronomy.swin.edu.au/-pbourke/prolection/coords>.
Boyd et al., "Three Dimensional Diagnosis and Orthodontic Treatment of Complex Malocclusions With the lnvisalipn Appliance," Semin. Orthod., 7(4):274-293 (Dec. 2001).
Brandestini et al., "Computer Machined Ceramic Inlays: In Vitro Marginal Adaptation," J. Dent. Res. Special Issue, Abstract 305, vol. 64, p. 208 (1985).
Brook et al., "An Image Analysis System for the Determination of Tooth Dimensions from Study Casts: Comparison with Manual Measurements of Mesio-distal Diameter," J. Dent. Res., 65(3):428-431 (Mar. 1986).
Burstone et al., Precision Adjustment of the Transpalatal Lingual Arch: Computer Arch Form in Predetermination, Am, Journal of Orthodontics, vol. 79, No. 2 (Feb. 1981), pp. 115-133.
Burstone (interview), "Dr. Charles J. Burstone on The Uses of the Computer in Orthodontic Practice (Part 1)," J. Clin. Orthod., 13(7):442-453 (Jul. 1979).
Burstone (interview), "Dr. Charles J. Burstone on the Uses of the Computer in Orthodontic Practice (Part 2)," J. Clin. Orthod., 13(8):539-551 (Aug. 1979).
Cardinal Industrial Finishes, Powder Coatings information posted at<http://www.cardinalpaint.com> on Aug. 25, 2000, 2 pages.
Carnaghan, "An Alternative to Holograms for the Portrayal of Human Teeth," 4th Int'l. Conf. on Holographic Systems, Components and Applications, Sep. 15, 1993, pp. 228-231.
Chaconas et al., "The DigiGraph Work Station, Part 1, Basic Concepts," JCO, pp. 360-367 (Jun. 1990).
Chafetz et al., "Subsidence of the Femoral Prosthesis, A Stereophotogrammetric Evaluation," Clin. Orthop. Relat. Res., No. 201, pp. 60-67 (Dec. 1985).
Chiappone, (1980). Constructing the Gnathologic Setup and Positioner, J. Clin. Orthod, vol. 14, pp. 121-133.
Cottingham, (1969). Gnathologic Clear Plastic Positioner, Am. J. Orthod, vol. 55, pp. 23-31.
Crawford, "CAD/CAM in the Dental Office: Does It Work?", Canadian Dental Journal, vol. 57, No. 2, pp. 121-123 (Feb. 1991).
Crawford, "Computers in Dentistry: Part 1 CAD/CAM: The Computer Moves Chairside, Part 2 F. Duret—A Man with a Vision, Part 3 The Computer Gives New Vision—Literally, Part 4 Bytes 'N Bites—The Computer Moves from the Front Desk to the Operatory," Canadian Dental Journal, vol. 54 (9), pp. 661-666 (1988).
Crooks, "CAD/CAM Comes to USC," USC Dentistry, pp. 14-17 (Spring 1990).
Cureton, Correcting Malaligned Mandibular Incisors with Removable Retainers, J. Clin. Orthod, vol. 30, No. 7 (1996) pp. 390-395.
Curry et al., "Integrated Three-Dimensional Craniofacial Mapping at the Craniofacial Research Instrumentation Laboratory/University of the Pacific," Semin. Orthod., 7(4):258-265 (Dec. 2001).
Cutting et a/., "Three-Dimensional Computer-Assisted Design of Craniofacial Surgical Procedures: Optimization and Interaction with Cephalometric and CT-Based Models," Plast. 77(6):877-885 (Jun. 1986).
DCS Dental AG, "The CAD/CAM 'DCS Titan System' for Production of Crowns/Bridges," DSC Production AG, pp. 1-7 (Jan. 1992).
Definition for gingiva. Dictionary.com p. 1-3. Retrieved from the internet Nov. 5, 2004< http://reference.com/search/search?q=gingiva>.
Defranco et al., "Three-Dimensional Large Displacement Analysis of Orthodontic Appliances," J. Biomechanics, 9:793-801 (1976).
Dental Institute University of Zurich Switzerland, Program for International Symposium JD on Computer Restorations: State of the Art of the CEREC-Method, May 1991, 2 pages total.
Dentrac Corporation, Dentrac document, pp. 4-13 (1992).
DENT-X posted on Sep. 24, 1998 at< http://www.dent-x.com/DentSim.htm>, 6 pages.
Doyle, "Digital Dentistry," Computer Graphics World, pp. 50-52, 54 (Oct. 2000).
DuraClearTM product information, Allesee Orthodontic Appliances-Pro Lab, 1 page (1997).
Duret et al., "CAD/CAM Imaging in Dentistry," Curr. Opin. Dent., 1:150-154 (1991).
Duret et al, "CAD-CAM in Dentistry," J. Am. Dent. Assoc. 117:715-720 (Nov. 1988).
Duret, "The Dental CAD/CAM, General Description of the Project," Hennson International Product Brochure, 18 pages total, Jan. 1986.
Duret, "Vers Une Prosthese Informatisee," (English translation attached), Tonus, vol. 75, pp. 55-57 (Nov. 15, 1985).
Economides, "The Microcomputer in the Orthodontic Office," JCO, pp. 767-772 (Nov. 1979).
Elsasser, Some Observations on the History and Uses of the Kesling Positioner, Am. J. Orthod. (1950) 36:368-374.
English translation of Japanese Laid-Open Publication No. 63-11148 to inventor T. Ozukuri (Laid-Open on Jan. 18, 1998) pp. 1-7.
Felton et al., "A Computerized Analysis of the Shape and Stability of Mandibular Arch Form," Am. J. Orthod. Dentofacial Orthop., 92(6):478-483 (Dec. 1987).
Friede et al., "Accuracy of Cephalometric Prediction in Orthognathic Surgery," Abstract of Papers, J. Dent. Res., 70:754-760 (1987).
Futterling et a/., "Automated Finite Element Modeling of a Human Mandible with Dental Implants," JS WSCG '98—Conference Program, retrieved from the Internet:< http://wscg.zcu.cz/wscg98/papers98/Strasser 98.pdf>, 8 pages.
Gao et al., "3-D element Generation for Multi-Connected Complex Dental and Mandibular Structure," Proc. Intl Workshop on Medical Imaging and Augmented Reality, pp. 267-271 (Jun. 12, 2001).
Gim-Alldent Deutschland, "Das DUX System: Die Technik," 2 pages total (2002).
Gottleib et al., "JCO Interviews Dr. James A. McNamura, Jr., on the Frankel Appliance: Part 2: Clinical 1-1 Management," J. Clin. Orthod., 16(6):390-407 (Jun. 1982).
Grayson, "New Methods for Three Dimensional Analysis of Craniofacial Deformity, Symposium: JW Computerized Facial Imaging in Oral and Maxiiofacial Surgery," AAOMS, 3 pages total, (Sep. 13, 1990).
Guess et al., "Computer Treatment Estimates in Orthodontics and Orthognathic Surgery," JCO, pp. 262-28 (Apr. 1989).
Heaven et a/., "Computer-Based Image Analysis of Artificial Root Surface Caries," Abstracts of Papers, J. Dent. Res., 70:528 (Apr. 17-21, 1991).
Highbeam Research, "Simulating Stress Put on Jaw," Tooling & Production [online], Nov. 1996, n pp. 1-2, retrieved from the Internet on Nov. 5, 2004, URL http://static.highbeam.com/t/toolingampproduction/november011996/simulatingstresspu tonfa . . . >.
Hikage, "Integrated Orthodontic Management System for Virtual Three-Dimensional Computer Graphic Simulation and Optical Video Image Database for Diagnosis and Treatment Planning", Journal of Japan KA Orthodontic Society, Feb. 1987, English translation, pp. 1-38, Japanese version, 46(2), pp. 248-269 (60 pages total).
Hoffmann, et al., "Role of Cephalometry for Planning of Jaw Orthopedics and Jaw Surgery Procedures," (Article Summary in English, article in German), Informatbnen, pp. 375-396 (Mar. 1991).
Hojjatie et al., "Three-Dimensional Finite Element Analysis of Glass-Ceramic Dental Crowns," J. Biomech., 23(11):1157-1166 (1990).

(56) References Cited

OTHER PUBLICATIONS

Huckins, "CAD-CAM Generated Mandibular Model Prototype from MRI Data," AAOMS, p. 96 (1999).
Important Tip About Wearing the Red White & Blue Active Clear Retainer System, Allesee Orthodontic Appliances—Pro Lab, 1 page 1998).
Ivoclar Vivadent Ltd., "IPS Empress: More Detail", and "The Ultimate in Metal Free Esthelics", [http://www.ivoclarco.uk/technician/nonmeta12.html], p. 1, [http://www.ivoclarco.uk/technician/nonmeta12.html], pp. 1-2. Nov. 7, 2004.
JCO Interviews, Craig Andreiko, DDS, MS on the Elan and Orthos Systems, JCO, pp. 459-468 (Aug. 1994).
JCO Interviews, Dr. Homer W. Phillips on Computers in Orthodontic Practice, Part 2, JCO. 1997; 1983:819-831.
Jerrold, "The Problem, Electronic Data Transmission and the Law," AJO-DO, pp. 478-479 (Apr. 1988).
Jones et al., "An Assessment of the Fit of a Parabolic Curve to Pre- and Post-Treatment Dental Arches," Br. J. Orthod., 16:85-93 (1989).
JP Faber et al., "Computerized Interactive Orthodontic Treatment Planning," Am. J. Orthod., 73(1):36-46 (Jan. 1978).
Kamada et.al., Case Reports on Tooth Positioners Using LTV Vinyl Silicone Rubber, J. Nihon University School of Dentistry (1984) 26(1): 11-29.
Kamada et.al., Construction of Tooth Positioners with LTV Vinyl Silicone Rubber and Some Case KJ Reports, J. Nihon University School of Dentistry (1982) 24(1):1-27.
Kanazawa et al., "Three-Dimensional Measurements of the Occlusal Surfaces of Upper Molars in a Dutch Population," J. Dent Res., 63(11):1298-1301 (Nov. 1984).
Kesling, Coordinating the Predetermined Pattern and Tooth Positioner with Conventional Treatment, KN Am. J. Orthod. Oral Surg. (1946) 32:285-293.
Kesling et al., The Philosophy of the Tooth Positioning Appliance, American Journal of Orthodontics and Oral surgery. 1945; 31:297-304.
Kleeman et al., The Speed Positioner, J. Clin. Orthod. (1996) 30:673-680.
Kochanek, "Interpolating Splines with Local Tension, Continuity and Bias Control," Computer Graphics, ri 18(3):33-41 (Jul. 1984).
KM Oral Surgery (1945) 31:297-30.
Kunii et al., "Articulation Simulation for an Intelligent Dental Care System," Displays 15:181-188 (1994).
Kuroda et al., Three-Dimensional Dental Cast Analyzing System Using Laser Scanning, Am. J. Orthod. Dentofac. Orthop. (1996) 110:365-369.
Laurendeau, et al., "A Computer-Vision Technique for the Acquisition and Processing of 3-D Profiles of 7 KR Dental Imprints: An Application in Orthodontics," IEEE Transactions on Medical Imaging, 10(3):453-461 (Sep. 1991).
Leinfelder, et al., "A New Method for Generating Ceramic Restorations: a CAD-CAM System," J. Am. 1-1 Dent. Assoc., 118(6):703-707 (Jun. 1989).
Manetti, et al., "Computer-Aided Cefalometry and New Mechanics in Orthodontics," (Article Summary in English, article in German), Fortschr Kieferorthop. 44, 370-376 (Nr. 5), 1983.
Marshall, et al. U.S. Appl. No. 60/631,897, filed Nov. 30, 2004.
McCann, "Inside the ADA," J. Amer. Dent. Assoc., 118:286-294 (Mar. 1989).
McNamara et al., "Invisible Retainers," J. Cfin. Orthod., pp. 570-578 (Aug. 1985).
McNamara et al., Orthodontic and Orthopedic Treatment in the Mixed Dentition, Needham Press, pp. 347-353 (Jan. 1993).
Moermann et al., "Computer Machined Adhesive Porcelain Inlays: Margin Adaptation after Fatigue Stress," IADR Abstract 339, J. Dent. Res., 66(a):763 (1987).
Moles, "Correcting Mild Malalignments—As Easy As One, Two, Three," AOA/Pro Corner, vol. 11, No. 1, 2 pages (2002).
Mormann et al., "Marginale Adaptation von adhasuven Porzellaninlays in vitro," Separatdruck aus: Schweiz. Mschr. Zahnmed. 95: 1118-1129, 1985.

Nahoum, "The Vacuum Formed Dental Contour Appliance," N. Y. State Dent. J., 30(9):385390 (Nov. 1964).
Nash, "CEREC CAD/CAM Inlays: Aesthetics and Durability in a Single Appointment," Dent. Today, 9(8):20, 22-23 (Oct. 1990).
Nishiyama et al., "A New Construction of Tooth Repositioner by LTV Vinyl Silicone Rubber," J. Nihon Univ. Sch. Dent., 19(2):93-102 (1977).
Paul et al., "Digital Documentation of Individual Human Jaw and Tooth Forms for Applications in Orthodontics, Oral Surgery and Forensic Medicine" Proc. of the 24th Annual Conf. of the IEEE Industrial Electronics Society (IECON '98), Sep. 4, 1998, pp. 2415-2418.
Pinkham, "Foolish Concept Propels Technology," Dentist, 3 pages total, Jan./Feb. 1989.
Pinkham, "Inventor's CAD/CAM May Transform Dentistry," Dentist, 3 pages total, Sep. 1990.
Ponitz, "Invisible Retainers," Am. J. Orthod., 59(3):266-272 (Mar. 1971).
PROCERA Research Projects, "PROCERA Research Projects 1993—Abstract Collection," pp. 3-7; 28 (1993).
Proffit et al., Contemporary Orthodontics, (Second Ed.), Chapter 15, Mosby Inc., pp. 470-533 (Oct. 1993.
Raintree Essix & ARS Materials, Inc., Raintree Essix, Technical Magazine Table of contents and Essix Appliances,< http:// www.essix.com/magazine/defaulthtml> Aug. 13, 1997.
Redmond et al., "Clinical Implications of Digital Orthodontics," Am. J. Orthod. Dentofacial Orthop., 117(2):240-242 (2000).
Rekow, "A Review of the Developments in Dental CAD/CAM Systems," (contains references to Japanese efforts and content of the papers of particular interest to the clinician are indicated with a one line summary of their content in the bibliography), Curr. Opin. Dent., 2:25-33 (Jun. 1992).
Rekow, "CAD/CAM in Dentistry: A Historical Perspective and View of the Future," J. Can. Dent. Assoc., 58(4):283, 287-288 (Apr. 1992).
Rekow, "Computer-Aided Design and Manufacturing in Dentistry: A Review of the State of the Art," J. Prosthet. Dent., 58(4):512-516 (Oct. 1987).
Rekow, "Dental CAD-CAM Systems: What is the State of the Art?", J. Amer. Dent. Assoc., 122:43-48 1991.
Rekow et al., "CAD/CAM for Dental Restorations—Some of the Curious Challenges," IEEE Trans. Biomed. Eng., 38(4):314-318 (Apr. 1991).
Rekow et al., "Comparison of Three Data Acquisition Techniques for 3-D Tooth Surface Mapping," Annual International Conference of the IEEE Engineering in Medicine and Biology Society, 13(1):344-345 1991.
Rekow, "Feasibility of an Automated System for Production of Dental Restorations, Ph.D. Thesis," Univ. of Minnesota, 244 pages total, Nov. 1988.
Richmond et al., "The Development of a 3D Cast Analysis System," Br. J. Orthod., 13(1):53-54 (Jan. 1986).
Richmond et al., "The Development of the PAR Index (Peer Assessment Rating): Reliability and Validity," Eur. J. Orthod., 14:125-139 (1992).
Richmond, "Recording the Dental Cast in Three Dimensions," Am. J. Orthod. Dentofacial Orthop., 92(3):199-206 (Sep. 1987).
Rudge, "Dental Arch Analysis: Arch Form, A Review of the Literature," Eur. J. Orthod., 3(4):279-284 1981.
Sakuda et al., "Integrated Information-Processing System in Clinical Orthodontics: An Approach with Use of a Computer Network System," Am. J. Orthod. Dentofacial Orthop., 101(3): 210-220 (Mar. 1992).
Schellhas et al., "Three-Dimensional Computed Tomography in Maxillofacial Surgical Planning," Arch. Otolamp!. Head Neck Sur9., 114:438-442 (Apr. 1988).
Schroeder et al., Eds. The Visual Toolkit, Prentice Hall PTR, New Jersey (1998) Chapters 6, 8 & 9, (pp. 153-210,309-354, and 355-428, respectively.
Shilliday, (1971). Minimizing finishing problems with the mini-positioner, Am. J. Orthod. 59:596-599.
Siemens, "CEREC—Computer-Reconstruction," High Tech in der Zahnmedizin, 14 pages total (2004).

(56) References Cited

OTHER PUBLICATIONS

Sinclair, "The Readers' Corner," J. Clin. Orthod., 26(6):369-372 (Jun. 1992).

Sirona Dental Systems GmbH, CEREC 3D, Manuel utiiisateur, Version 2.0X (in French), 2003,114 pages total.

Stoll et al., "Computer-aided Technologies in Dentistry," (article summary in English, article in German), Dtsch Zahna'rztl Z 45, pp. 314-322 (1990).

Sturman, "Interactive Keyframe Animation of 3-D Articulated Models," Proceedings Graphics Interface '84, May-Jun. 1984, pp. 35-40.

The Choice Is Clear: Red, White & Blue . . . The Simple, Affordable, No-Braces Treatment, Allesee HI Orthodontic Appliances—Pro Lab product information for doctors. http://ormco.com/aoa/appliancesservices/RWB/doctorhtml>, 5 pages (May 19, 2003).

The Choice is Clear: Red, White & Blue . . . The Simple, Affordable, No-Braces Treatment, Allesee HJ Orthodontic Appliances—Pro Lab product information for patients,< http://ormco.com/aoa/appliancesservices/RWB/patients.html>, 2 pages (May 19, 2003).

The Choice Is Clear: Red, White & Blue . . . The Simple, Affordable, No-Braces Treatment, Allesee Orthodontic Appliances—Pro Lab product information, 6 pages (2003).

The Red, White & Blue Way to Improve Your Smile! Allesee Orthodontic Appliances—Pro Lab product information for patients, 2 pages 1992.

Truax L., "Truax Clasp-Less(TM) Appliance System," Funct. Orthod., 9(5):22-4, 26-8 (Sep.-Oct. 1992).

Tru-Tain Orthodontic & Dental Supplies, Product Brochure, Rochester, Minnesota 55902, 16 pages total (1996).

U.S. Department of Commerce, National Technical Information Service, "Automated Crown Replication Using Solid Photography SM," Solid Photography Inc., Melville NY, Oct. 1977, 20 pages total.

U.S. Department of Commerce, National Technical Information Service, "Holodontography: An Introduction to Dental Laser Holography," School of Aerospace Medicine Brooks AFB Tex, Mar. 1973, 37 pages total.

U.S. Appl. No. 60/050,342, filed Jun. 20, 1997, 41 pages total.

Van Der Linden, "A New Method to Determine Tooth Positions and Dental Arch Dimensions," J. Dent. Res., 51(4):1104 (Jul.-Aug. 1972).

Van Der Linden et al., "Three-Dimensional Analysis of Dental Casts by Means of the Optocom," J. Dent. Res., p. 1100 (Jul.-Aug. 1972).

Van Der Zel, "Ceramic-Fused-to-Metal Restorations with a New CAD/CAM System," Quintessence Int., 24(11):769-778 (1993).

Varady et al., "Reverse Engineering of Geometric Models—An Introduction," Computer-Aided Design, 29(4):255-268,1997.

Verstreken et al., "An Image-Guided Planning System for Endosseous Oral Implants," IEEE Trans. Med. Imaging, 17(5):842-852 (Oct. 1998).

Warunek et al., Physical and Mechanical Properties of Elastomers in Orthodonic Positioners, Am J. Orthod. Dentofac. Orthop, vol. 95, No. 5, (May 1989) pp. 399-400.

Warunek et.al., Clinical Use of Silicone Elastomer Appliances, JCO (1989) XXIII(10):694-700.

Wells, Application of the Positioner Appliance in Orthodontic Treatment, Am. J. Orthodont. (1970) 58:351-366.

Williams, "Dentistry and CAD/CAM: Another French Revolution," J. Dent. Practice Admin., pp. 2-5 (Jan./Mar. 1987).

Williams, "The Switzerland and Minnesota Developments in CAD/CAM," J. Dent. Practice Admin., pp. 50-55 (Apr./Jun. 1987.

Wishan, "New Advances in Personal Computer Applications for Cephalometric Analysis, Growth Prediction, Surgical Treatment Planning and Imaging Processing," Symposium: Computerized Facial Imaging in Oral and Maxilofacial Surgery Presented on Sep. 13, 1990.

WSCG'98—Conference Program, "The Sixth International Conference in Central Europe on Computer Graphics and Visualization '98," Feb. 9-13, 1998, pp. 1-7, retrieved from the Internet on Nov. 5, 2004, URL<http://wscg.zcu.cz/wscg98/wscg98.h>.

Xia et al., "Three-Dimensional Virtual-Reality Surgical Planning and Soft-Tissue Prediction for Orthognathic Surgery," IEEE Trans. Inf. Technol. Biomed., 5(2):97-107 (Jun. 2001).

Yamamoto et al., "Optical Measurement of Dental Cast Profile and Application to Analysis of Three-Dimensional Tooth Movement in Orthodontics," Front. Med. Biol. Eng., 1(2):119-130 (1988).

Yamamoto et al., "Three-Dimensional Measurement of Dental Cast Profiles and Its Applications to Orthodontics," Conf. Proc. IEEE Eng. Med. Biol. Soc., 12(5):2051-2053 (1990).

Yamany et al., "A System for Human Jaw Modeling Using Intra-Oral Images," Proc. of the 20th Annual Conf. of the IEEE Engineering in Medicine and Biology Society, Nov. 1, 1998, vol. 2, pp. 563-566.

Yoshii, "Research on a New Orthodontic Appliance: The Dynamic Positioner (D.P.); I. The D.P. Concept and Implementation of Transparent Silicone Resin (Orthocon)," Nippon Dental Review, 452:61-74 (Jun. 1980).

Yoshii, "Research on a New Orthodontic Appliance: The Dynamic Positioner (D.P.); II. The D.P. Manufacturing Procedure and Clinical Applications," Nippon Dental Review, 454:107-130 (Aug. 1980).

Yoshii, "Research on a New Orthodontic Appliance: The Dynamic Positioner (D.P.); III. The General Concept of the D.P. Method and Its Therapeutic Effect, Part 1, Dental and Functional Reversed Occlusion Case Reports," Nippon Dental Review, 457:146-164 (Nov. 1980).

Yoshii, "Research on a New Orthodontic Appliance: The Dynamic Positioner (D.P.); III.—The General Concept of the D.P. Method and Its Therapeutic Effect, Part 2. Skeletal Reversed Occlusion Case Reports," Nippon Dental Review, 458:112-129 (Dec. 1980).

You May Be a Candidate for This Invisible No-Braces Treatment, Allesee Orthodontic Appliances—Pro Lab product information for patients, 2 pages (2002).

SYSTEM AND METHOD FOR MANUFACTURING A DENTAL PROSTHESIS AND A DENTAL PROSTHESIS MANUFACTURED THEREBY

CROSS-REFERENCE

This application is a continuation application of U.S. patent application Ser. No. 14/533,033, filed Nov. 4, 2014, now U.S. Pat. No. 10,059,059, issued Aug. 28, 2018, which is a continuation application of U.S. patent application Ser. No. 12/659,385, filed Mar. 8, 2010, now U.S. Pat. No. 8,909,363, issued Dec. 9, 2014, which is a continuation application of U.S. patent application Ser. No. 11/783,149, filed Apr. 6, 2007, now U.S. Pat. No. 7,689,310, issued Mar. 30, 2010, which is a continuation application of U.S. patent application Ser. No. 11/290,449, filed Dec. 1, 2005, now U.S. Pat. No. 7,236,842, issued Jun. 26, 2007, claiming the benefit under 35 U.S.C. 119(e) of U.S. Provisional Patent Application No. 60/632,350, filed Dec. 2, 2004, the contents of each of which are hereby incorporated by reference in their entireties.

FIELD OF INVENTION

This invention relates to teeth restoration, specifically to a system and method for fabricating dental prostheses, and to dental prostheses made thereby.

BACKGROUND OF THE INVENTION

The manufacture of dental prostheses such as crowns and bridges needs to be as precise as possible in order to ensure that, externally, the prosthesis fits within the area of the oral cavity assigned thereto, while also fitting properly onto the preparation. At the same time, it may sometimes be desired to have a number of layers in order to provide the prosthesis with a natural-looking appearance, in which inner layers may be more opaque than outer layers, for example, or contain a mosaicing of differently colored patches, and/or wherein each layer may be made from a different material.

Manual manufacturing methods for dental prostheses typically require a number of "fitting and fixing" cycles in order to ensure that the crown is properly dimensioned before finally fixing the prosthesis to the preparation in the intraoral cavity.

CNC-based methods for manufacturing dental prostheses are known and represent a significant improvement in automating the manufacturing process to provide a high degree of dimensional accuracy. For example, in U.S. Pat. No. 4,663,720 and in U.S. Pat. No. 5,027,281, material is removed from a massive block of material by means of a CNC milling machine, and the machining paths are calculated from a 3D numerical model of prosthesis. In U.S. Pat. No. 4,937,928, a dental prosthesis is manufactured by successively applying a number of layers of prosthesis material on a model in the shape of the part of the teeth where the prosthesis is to be provided. After each layer is applied, the workpiece is worked by a CNC tool controlled by a CAD/CAM system. In U.S. Pat. No. 5,378,154, a similar method is used for forming layers of material onto a preparation, machining each layer along paths that follow three dimensional irregularly spaced curved lines.

SUMMARY OF THE INVENTION

The present invention is directed to a method for manufacturing a dental prosthesis, comprising:

(a) providing at least one coping adapted for implantation at a dental site, the or each said at least one coping having a corresponding external surface;

(b) providing a three-dimensional (3D) virtual model of said dental prosthesis having at least one virtual internal surface, the or each said at least one virtual internal surface being substantially complementary to a corresponding said external surface of the or each said coping, respectively;

(c) generating computerized numerical control (CNC) instructions corresponding to said 3D model;

(d) producing a set of wax models, comprising at least one wax model, corresponding to said prosthesis in association with said at least one coping by means of material removal operations based on said CNC instructions;

(e) producing a dental prosthesis on said coping from said set of wax models.

The method may be applied for the fabrication of a single layered crown prosthesis, wherein said set of wax models comprises a wax model of said prosthesis substantially corresponding to said 3D virtual model. Alternatively, the method may be applied for the fabrication of a multi-layered crown prosthesis, wherein said set of wax models comprises a wax model of each layer of said prosthesis substantially corresponding to virtual layers created in said 3D virtual model.

Alternatively, the method may be applied for the fabrication of a single layered bridge prosthesis, wherein said set of wax models comprises a wax model of said prosthesis substantially corresponding to said 3D virtual model. Alternatively, the method may be applied for the fabrication of a multi-layered bridge prosthesis, wherein said set of wax models comprises a wax model of each layer of said prosthesis substantially corresponding to virtual layers created in said 3D virtual model. In such cases, said 3D virtual model comprises two said virtual internal surfaces, each substantially complementary to a corresponding said external surface of one or another of two said copings.

Step (a) may be performed using a lost wax process, or via a direct machining process, for example.

Typically, step (b) comprises providing a three-dimensional (3D) digital data relating to the patient's dentition, said 3D data including data representative of the surface topology of said preparation and its surroundings. Step (b) may be performed using a suitable optical scanner, such as for example comprises a probe for determining three dimensional structure by confocal focusing of an array of light beams, and typically performed directly on the intraoral cavity comprising said preparation. Alternatively the digital data of step (b) is obtained from a virtual model of a prosthesis designed for said preparation. Typically, in step (b) an external surface of the virtual model is created based on predetermined criteria, which may relate for example to providing adequate mechanical strength for the prosthesis, and/or to providing a natural-looking appearance to the prosthesis.

Step (e) may be carried out according to a lost wax process, and the dental prosthesis may be made from a suitable metal and/or from a suitable ceramic material.

When the prosthesis comprises a plurality of layers, the set of wax models comprises a corresponding plurality of wax models, an innermost said wax model being formed with respect to said at least one coping, and successive wax models being formed in turn on a previously formed layer of the prosthesis based on a corresponding said wax model.

The present invention also relates to a dental prosthesis, fabricated according to the method of the invention.

The present invention is also directed to a method for the fabrication of a set of wax models, comprising at least one wax model, to be used for the fabrication of a dental prosthesis of at least one tooth to be fitted over at least one tooth preparation, comprising:

(a) providing at least one coping adapted for implantation at a dental site, the or each said at least one coping having a corresponding external surface;

(b) providing a three-dimensional (3D) virtual model of said dental prosthesis having at least one virtual internal surface, the or each said at least one virtual internal surface being substantially complementary to a corresponding said external surface of the or each said coping, respectively;

(c) generating computerized numerical control (CNC) instructions corresponding to said 3D model;

(d) producing a set of wax models, comprising at least one wax model, corresponding to said prosthesis in association with said at least one coping by means of material removal operations based on said CNC instructions.

The present invention also relates to a set of wax models, fabricated according to the method of the invention.

The present invention is also directed to a system for manufacturing a dental prosthesis, comprising:

(a) first fabricating system for providing at least one coping adapted for implantation at a dental site, the or each said at least one coping having a corresponding external surface;

(b) first computer based system for providing a three-dimensional (3D) virtual model of said dental prosthesis having at least one virtual internal surface, the or each said at least one virtual internal surface being substantially complementary to a corresponding said external surface of the or each said coping, respectively;

(c) second computer based system for generating computerized numerical control (CNC) instructions corresponding to said 3D model;

(d) second fabricating system for producing a set of wax models, comprising at least one wax model, corresponding to said prosthesis in association with said at least one coping by means of material removal operations based on said CNC instructions;

(e) third fabricating system for producing a dental prosthesis on said coping from said set of wax models.

Optionally, the first and second computer systems may be integrated or may be the same computer system, or alternatively they may comprise different systems. Optionally, the first and second, or the first and third, or the second and third, or the first and second and third fabricating systems may be integrated or may be the same fabricating system, or alternatively they may comprise different systems.

The present invention is also directed to a system for the fabrication of a set of wax models, comprising at least one wax model, to be used for the fabrication of a dental prosthesis of at least one tooth to be fitted over at least one tooth preparation, comprising:

(a) first fabricating system for providing at least one coping adapted for implantation at a dental site, the or each said at least one coping having a corresponding external surface;

(b) first computer based system for providing a three-dimensional (3D) virtual model of said dental prosthesis having at least one virtual internal surface, the or each said at least one virtual internal surface being substantially complementary to a corresponding said external surface of the or each said coping, respectively;

(c) second computer based system for generating computerized numerical control (CNC) instructions corresponding to said 3D model;

(d) second fabricating system for producing a set of wax models, comprising at least one wax model, corresponding to said prosthesis in association with said at least one coping by means of material removal operations based on said CNC instructions.

Optionally, the first and second computer systems may be integrated or comprise the same computer system, or alternatively they may be different systems. Optionally, the first and second fabricating systems may be integrated or may be the same fabricating system, or alternatively they may comprise different systems.

In each aspect of the invention outlined above, step (d) involves providing a set of wax models, comprising at least one wax model, corresponding to the prosthesis in association with the at least one coping by means of material removal operations based on said CNC instructions. Step (d) may be executed by any suitable material removal operation, for example each successive wax model may be machined (for example by milling) from an external layer of wax that is deposited on the previous prosthesis layer, which may be the coping itself.

The term "prosthesis" is herein taken to include onlays, such as crowns and bridges, for example, and inlays, such as caps, for example, and any other artificial partial or complete denture. Generally, where one or more copings are used, the term "prosthesis" is used herein to refer to the artificial structure replacing a dental structure, and excluding the one or more copings.

The terms "tool" and "machining tool" are taken herein to include any tool that is adapted for material removal, and may include inter alia mechanical tools such as drills for example, laser tools such as for example laser drills or cutters, ultrasonic tools such as for example ultrasonic cutters, and so on. Preferably, the machining paths and material removal characteristics of such tools can be finely controlled, typically by computer means.

The term "layer" is used herein to a thickness of material partially or fully overlying a coping, as well as to a thickness of material that may be partially or fully overlying or underlying another layer of material.

Herein, "dental material" refers to any material associated with dental structures of the intra oral cavity, including but limited to natural dental materials such as for example enamel, dentine, pulp, dental roots, and non-natural dental materials such as for example metallic and non-metallic filings, restorations, crowns, bridges, copings, preparations, and so on.

Herein, "dental clinic" refers to the interface between a dental practitioner and a patient, and thus includes any physical entity, in particular a clinic, in which there is interaction between a dental patient and a dental practitioner. While "dental practitioner" and "care provider" typically refer herein to a dentist, doctor or dental technician, it also includes herein all other caregivers that may interact with a dental patient during the course of a dental treatment. While "dental patient" or "patient" typically refer to a person requiring the dental services of a dental practitioner, it also includes herein any person regarding whom it is desired to create a 3D numerical model of the intra oral cavity thereof, for example for the purpose of practicing the same or for carrying out research.

The term "dental site" is herein taken to include any part of the intraoral cavity in which it is desired to implant a dental prosthesis, and includes, for example, the area vacated by one or more teeth such as to expose one or more preparations and/or one or more artificial pivots or the like to enable a crown or bridge prosthesis to be fitted thereat. Dental site also includes teeth in which some dental material has been removed and are to receive a restoration including onlays, inlays, and any other artificial partial or complete denture.

While the term "preparation" typically refers to the stump (including the finish line and shoulder) that is left of the tooth that is to be replaced by the prosthesis—typically a crown or bridge—and on which the prosthesis is to be mounted, the term herein also includes implants such as for example artificial stumps, pivots, cores and posts, or other devices that may be implanted in the intraoral cavity forming a basis for implanting the prosthesis.

The term "prosthodontic procedure" refers, inter alia, to any procedure involving the intraoral cavity and directed to the design, manufacture or installation of a dental prosthesis at a dental site within the intraoral cavity, or a real or virtual model thereof, or directed to the design and preparation of the dental site to receive such a prosthesis.

The term "numerical entity" is used herein synonymously with virtual model, 3D model, and other such terms, and relates to a virtual representation of a real object, typically of a dentition or at least a part of intraoral cavity, or of a real model thereof, for example.

The term "dental coping" as used herein refers to a support structure for a crown, i.e. structure that cups only one tooth, as well as a support structure for a bridge, i.e. structure that cups more than one tooth. The dental coping may be fabricated from any suitable materials, including but not limited to metal, ceramo-metal materials, ceramics, etc.

The 3D digital data may be obtained by a number of ways known per se. For example, such digital data may be obtained in a manner as described in WO 00/08415, U.S. Patent Publication No. 2002/0137011 or in any of U.S. Pat. Nos. 6,099,314 and 6,334,853, or any combination thereof. The 3D data includes the surface topology of the preparation, as well as its surroundings. Furthermore, such 3D digital data may also comprise other data, for example, data that was added by the orthodontist or a dental technician, such as the preparation's finish line.

The present invention provides, in its first aspect, a method and system for fabricating a dental prosthesis of at least one tooth which is to be fitted over t least one tooth preparation.

By way of example, the coping used in connection with the invention may be designed primarily on the basis of the surface topology of the preparation and other factors such as the coping wall's thickness, finish line data, etc.

The generation of the virtual 3D coping data may be automatic, manual or a combination thereof.

The term "wax" includes any material that is relatively hard and lends itself to machining, particularly milling, while having a sufficiently low melting point and appropriate kinematic viscosity that renders it suitable for use in a lost wax process or the like.

The wax that should be used in accordance with the invention is hard and durable that lends itself to milling in a milling machine. Another requirement of the wax is that after melting, it should have a viscosity sufficiently low to be usable in a lost wax technique known per se in the art of metal casting.

A typical wax that can be used in accordance with the invention is such having a melting point and congealing point of 55-80° C. and a kinematic viscosity of less than 90 $m^2$ sec. at about 100° C.

According to the invention, a dental prosthesis may be made by externally machining successive layers of wax, each of which is formed on a previous prosthesis layer and/or on a coping. Each wax layer is used to form a mold in situ over the previous prosthesis layer/coping, and the appropriate prosthesis material is cast or otherwise molded to conform to the wax layer by the mold.

BRIEF DESCRIPTION OF THE DRAWINGS

In order to understand the invention and to see how it may be carried out in practice, a preferred embodiment will now be described, by way of non-limiting example only, with reference to the accompanying drawings, in which.

DETAILED DESCRIPTION OF THE INVENTION

Figure 1:
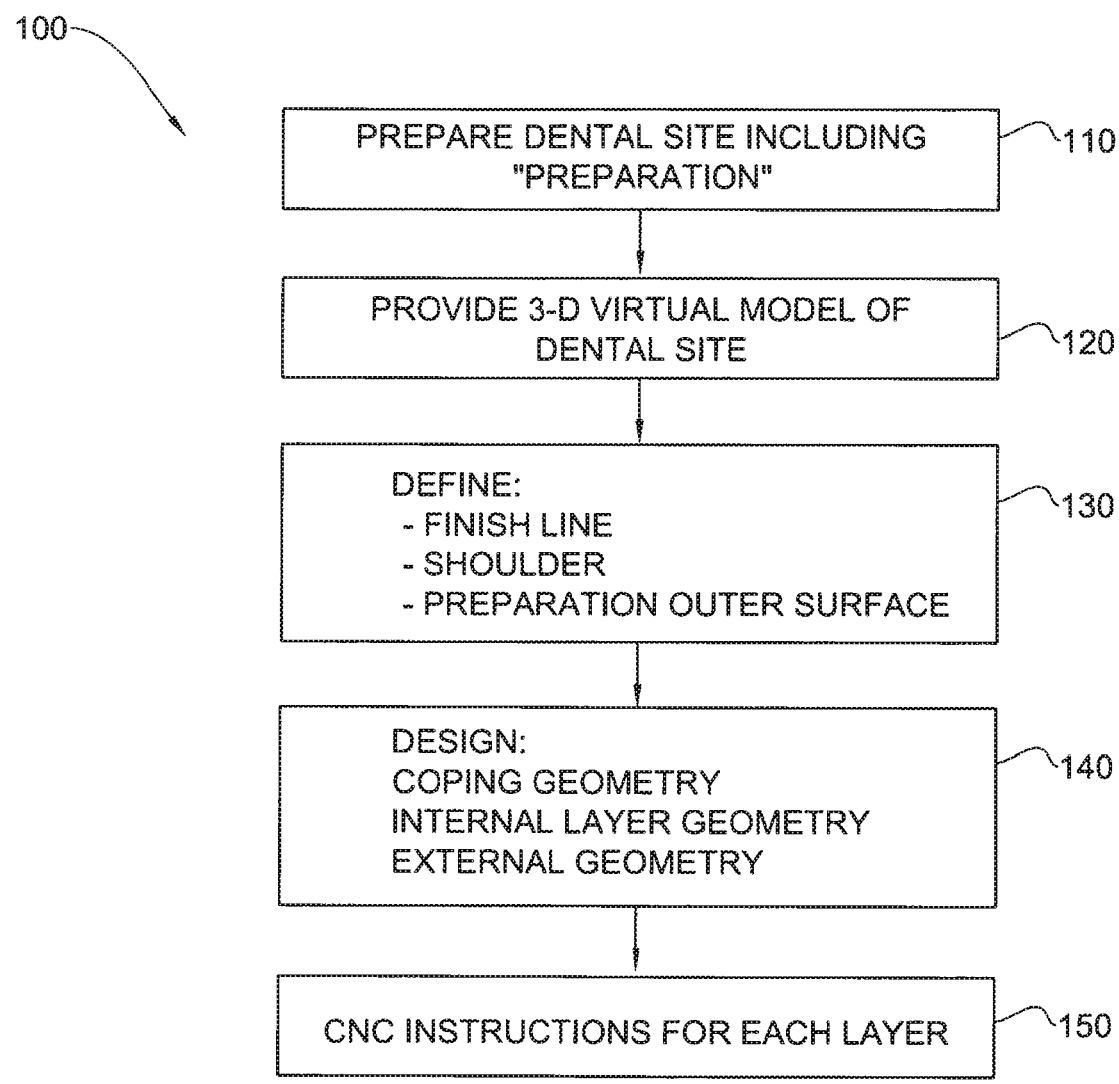
FIG. 1 is a flowchart illustrating various steps in a preprocess for generating CNC instructions for machining wax layers.
Figure 2:
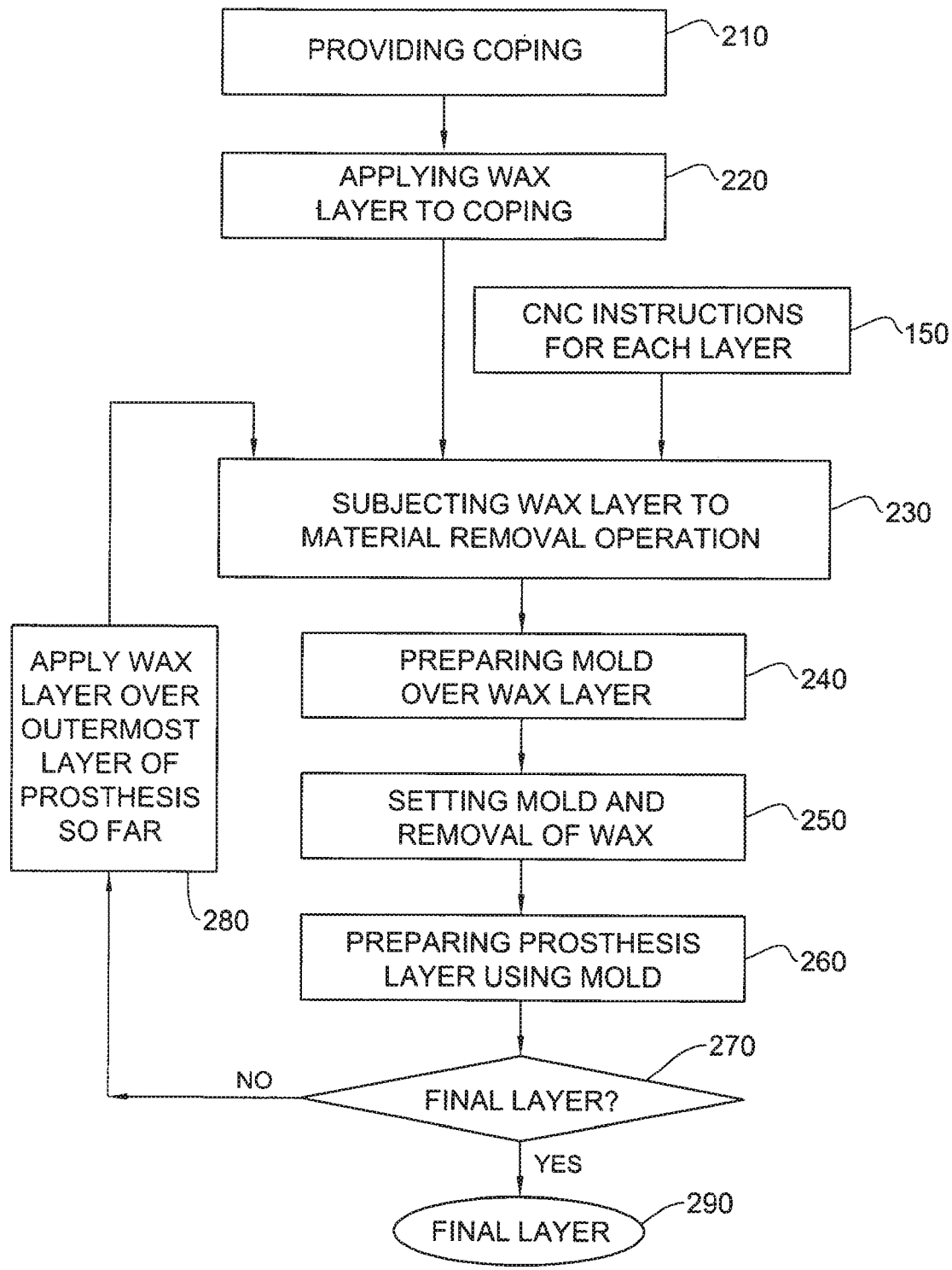
FIG. 2 is a flowchart illustrating various steps in a manufacturing process according to the invention.

FIGS. 1 and 2 schematically illustrate an exemplary implementation of the present invention for the fabrication of a dental prosthesis, typically carried out with the aid of a computer system, the operation of which will be explained hereinbelow.

In particular, FIG. 2 illustrates various steps of a process according to the invention for fabricating a dental prosthesis, described as follows in the context of a crown prosthesis, though the method applies, mutatis mutandis, to other prostheses, for example a crown:—

Step 210—a coping is provided, adapted for fitting onto the preparations at the dental site.

Step 220—a layer of wax is applied to the coping, this layer exceeding the envelope of the corresponding layer of the crown being fabricated.

Step 230—the wax layer is subjected to a CNC-controlled material removal operation to provide an outer surface that corresponds to a designed layer surface for the layer. CNC instructions for the material removal operation are provided in Step 150.

Step 240—the wax layer is invested in a material that solidifies onto the external side of the wax layer (still on the coping) and forms a mold (this stage is known as the "investment" stage).

Step 250—the combined structure is then heated such that the wax is burnt out, leaving a cavity into which the crown layer may be cast.

Step 260—the crown layer is cast in the mold using a metal, ceramic, or any other suitable material, and the mold material is removed.

Step 270—if this was the last layer required for the crown, Step 290 is implemented; otherwise, another layer is fabricated on the crown, continuing with Step 280.

Step 280—another layer of wax is applied, this time to the outermost layer of the crown fabricated so far, and steps 230 to 270 are performed based on the new wax layer and corresponding CNC instructions provided in step 150.

FIG. 1 illustrates various steps of a pre-process 100 that may be taken to provide suitable Computer Numerical Control (CNC) instructions that are used in step 150 of the process 200 of FIG. 2:—

Step 110—a preparation is formed at the dental site to receive the coping.

Step 120—a 3D virtual model of the dental site including the preparation is provided.

Step 130—occlusion data, finish line data, shoulder data (where applicable) and surface data of the preparation are obtained from the virtual model.

Step 140—the coping geometry and the geometry of each layer of the crown is designed.

Step 150—Computer Numerical Control instructions for each successive layer of the crown are prepared from the geometrical data in Step 140.

The above steps are now described in detail, first in the context of a crown prosthesis, and then in the context of a bridge prosthesis.

Figure 3:
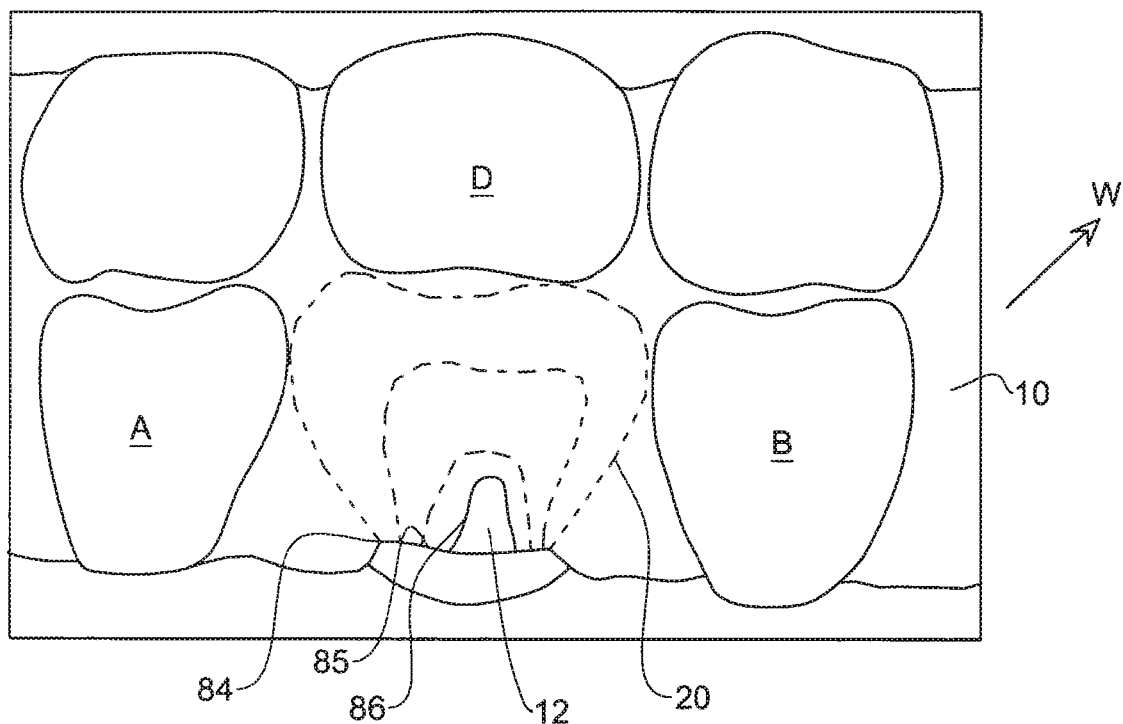
FIG. 3 schematically illustrates a dental site of an intraoral cavity in which it is desired to implant a crown prosthesis.

Referring to Step 110, FIG. 3 shows a section 10 of the intraoral cavity of a patient in which tooth prosthesis in the form of a crown (shown as dotted line 20) is to be fitted over tooth preparation 12, in the illustrated example—in patient's lower jaw. In the example of FIG. 3, the root and base of the missing tooth are sufficiently strong and healthy, and the care provider prepared the preparation 12 at the dental site for the crown typically by removing a portion of the enamel and dentin. If the tooth to be restored is severely decayed or weak, then it may be necessary to insert a metal implant or pivot (also known as cores or posts) by any one of a number of ways known per se.

According to the present invention, in step 110 a material removal operation is applied to a part of the intra oral cavity. Such a material removal operation may be executed using any suitable machining tool that is adapted for material removal, and may include inter alia mechanical tools such as drills for example, laser tools such as for example laser drills or cutters, ultrasonic tools such as for example ultrasonic cutters, and so on. At least a part of the material removal operation may comprise in some cases a loss of dental material, occurring, for example, via disease, mechanical forces such as a blow to the teeth for example, and so on.

Such a material removal operation is directed for the purpose of prosthodontic procedures, and thus includes the construction of a dental preparation at a dental site, so as to receive a prosthesis such as a crown, for example, or for providing a dental filling or restoration thereat.

Figure 4:
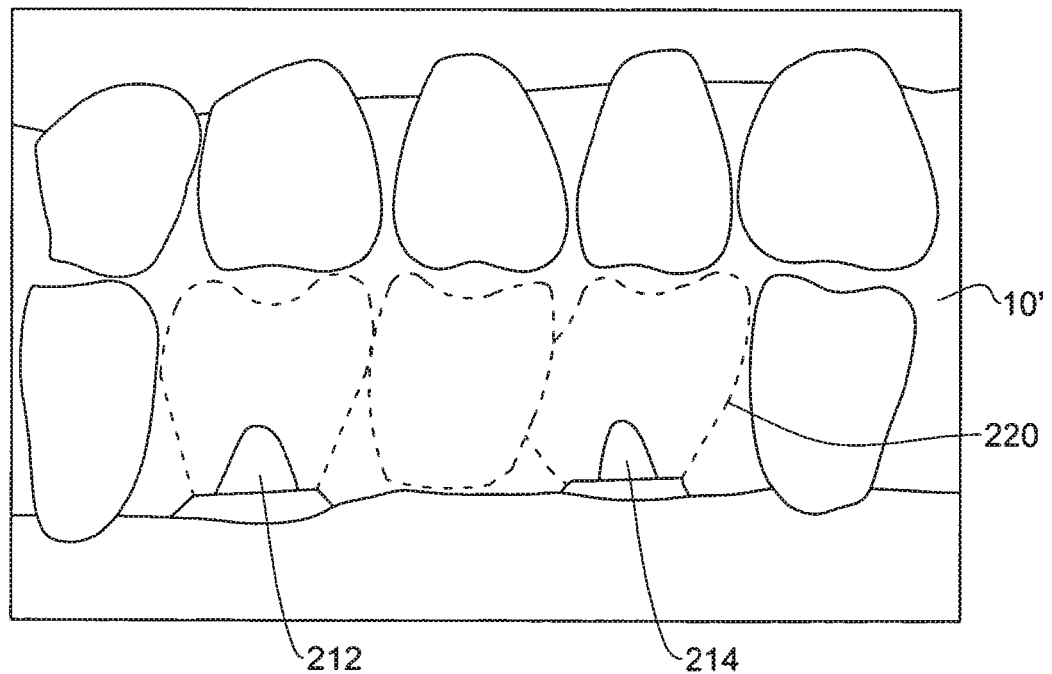
FIG. 4 schematically illustrates a dental site of an intraoral cavity in which it is desired to implant a bridge prosthesis.

FIG. 4 shows another section 10' of the intraoral cavity of a patient in which a bridge prosthesis (shown as dotted line 220) is to be implanted, fitted over a pair of preparations 212, 214 each similar to the preparation 12 described in connection with FIG. 3.

In Step 120, and referring again to FIG. 3, once the preparation 12 is completed, the 3D digitized data W of the intraoral cavity, including the dentition and associated anatomical structures of a patient is obtained, and thus suitable equipment for scanning a patient's teeth is used by the care provider to acquire the 3D data. The production of the virtual 3D working model of the preparation and its surroundings is known per-se. The 3D digitized data W, herein also referred to as a "virtual model" or "numerical entity" is representative of the three-dimensional surface of the preparation 12 and the surrounding areas of the intraoral cavity. The said numerical entity W is typically at least "three-dimensional", that is, each data point of the data set comprises at least three prime independent variables relating to spatial coordinates of a surface, typically defined along orthogonal Cartesian axes, x, y, z. Alternatively, these variables may be defined along polar axes or any other geometric system in which a surface may be described. Thus, the numerical entity W typically comprises a data set having a plurality of at least 3-dimensional arrays—(x, y, and z), wherein each array represents the x, y, z, geometrical coordinates.

Figure 5:
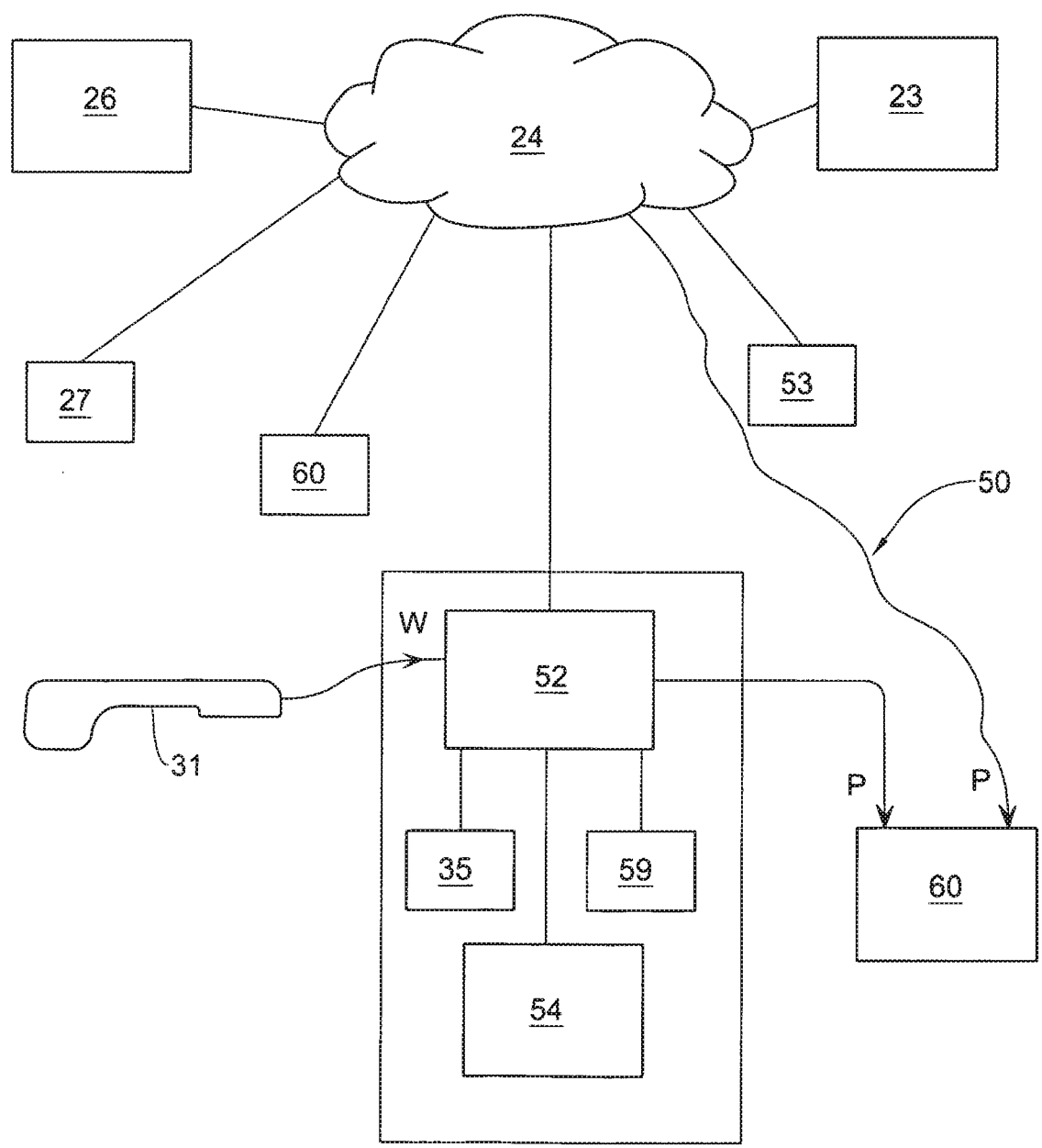
FIG. 5 schematically illustrates a system for generating CNC instructions for machining wax layers.

Any suitable means may be used to provide the numerical entity W. FIG. 5 illustrates the main elements of a system 50 for acquiring the 3D numerical entity, comprising a suitable scanner 31, a microprocessor or computer 52, and a display means 54. According to the invention, digitized three-dimensional (3D) information W of the patient's intra-oral cavity, or part thereof, 10 is created by the system 50 using scanner 31. Preferably, the 3D digitized data of the intraoral cavity is obtained, including the dentition and associated anatomical structures of a patient. The scanning means 31 may include, for example, a hand-held scanner that is used by the practitioner or other user to acquire the 3D data. Advantageously, a probe for determining three dimensional structure by confocal focusing of an array of light beams may be used, for example as manufactured under the name of PROSTHOCAD or as disclosed in WO 00/08415, the contents of which are incorporated herein in their entirety. Such a scanner 31 makes use of confocal imaging for providing an accurate three-dimensional representation of the target surface within the intra-oral cavity.

The system 50 is typically located at a dental clinic, and may be linked to one or more service centers 23 and/or dental labs 26, via a communication means or network such as for example the Internet or other suitable communications medium such as an intranet, local access network, public switched telephone network, cable network, satellite communication system, and the like, indicated by the cloud at 24. Optionally, it is also possible for some dental labs 26 to be linked to each other, via the same one or a different one of said communication medium, for example when such dental clinics or labs form part of a common commercial entity. Further optionally, such interlinked dental labs 26 may be further linked with other entities, for example a head clinic or head lab, comprising a centralized data base (not shown).

Typically, the design and manufacture of dental prosthesis may be eventually carried out at the dental lab 26 or at the service centre 23, or alternatively one or both of these activities may be shared between the two; in each case the design and manufacture are preferably based on the original 3D data of the oral cavity previously obtained. Thus, exchange of data between the system 50 and the dental lab 26 and/or service center 23 may be useful in creating an optimal geometry for a preparation being made in the intraoral cavity that enables the best prosthesis to be designed therefor, for example.

Alternatively, scanning of the dental cavity to provide the 3D data may be accomplished using a suitable apparatus, for example as disclosed in any one of U.S. Pat. Nos. 4,837,732, 4,611,288, 6,594,539, 6,402,707, 6,364,660, U.S. Patent Publication No. 2002/0028418, U.S. Patent Publication No. 2002/0058229, U.S. Pat. Nos. 5,652,709, 4,575,805, 5,733,126, 5,880,962, 4,742,464, 4,663,720, WO 02/071306 mutatis mutandis. The contents of these publications are incorporated herein in their entirety by reference thereto.

The 3D data obtained by the probe may then be stored in a suitable storage medium, for example a memory in a computer workstation, for further processing, as described herein.

Alternatively, a negative cast or impression is taken of the patient's teeth, in a manner known in the art, and this negative model and a positive cast is made from this model suitable for scanning. The positive cast may be scanned by any method known in the art, including using the aforesaid probe manufactured under the name of PROSTHOCAD or as disclosed in WO 00/08415. Alternatively, the negative model itself may be scanned.

Alternatively, a composite positive-negative model may be manufactured from the original negative model. Thereafter, the positive-negative model may be processed to obtain 3D digitized data, for example as disclosed in U.S. Pat. No. 6,099,314, assigned to the present assignee, and the contents of which are incorporated herein in their entirety.

Alternatively, the 3D digitized data may be obtained in any other suitable manner, including other suitable intra oral scanning techniques, based on optical methods, direct contact or any other means, applied directly to the patient's dentition or to a physical model thereof previously obtained. Alternatively, X-ray based, CT based, Mill based, or any other type of scanning of the patient's infra-oral cavity, or of a physical model thereof previously obtained, may be used. The physical model may be a positive model or a negative model of the dentition, and is obtainable using methods known per se in the art.

The additional 3D data that relates to the patient's dentition includes, inter-alia, information relating to the surrounding of the tooth to be restored, e.g. 3D representation of the patient's dentition, including the upper and lower jaws and their occlusion relationship. Such information is needed, e.g. for the design of the dental crown, and can be generated for example, as disclosed in U.S. Pat. Nos. 6,099,314 and 6,334,853.

Typically, the 3D digitized data W is obtained in a manner such that enables the data to be procured from the patient and analyzed according to the invention during a regular visit of a patient to a practitioner.

Optionally, the numerical entity or 3D digitized data W may further comprise a fourth prime independent variable, relating to a color parameter that is expressed numerically and is associated with the spatial coordinates. The color parameter may itself be comprised of independent prime color variables—for example relating to the red, blue and green (RGB) components associated with the color parameter. Alternatively, the color parameter may be expressed in terms of the Hue, Saturation and Intensity (HIS). Alternatively, any other color parameter may be used, including parameters that provide a measure of internal reflectance and translucency, or any other optical property of teeth. Thus, such a numerical entity typically comprises a data set having a plurality of 4-dimensional arrays—(x, y, z, c), wherein each array represents the x, y, z, geometrical coordinates, and wherein c represents the color value, of a point on a surface within the intra-oral cavity. Any suitable means may be used to provide this numerical entity. For example, a three-dimensional surface scanner with color capabilities may be used. Thus, advantageously, such a scanner makes use of confocal imaging for providing an accurate three-dimensional representation of the target surface within the intra-oral cavity. Color values may then added to each data point of this data set by obtaining a two-dimensional color image of the target surface, and then mapping the color values of the two-dimensional image onto the three-dimensional "image", for example as described in co-pending applications assigned to the present assignee, U.S. provisional Patent Application No. 60/580,109, entitled "METHOD FOR PROVIDING DATA ASSOCIATED WITH THE INTRAORAL CAVITY", and U.S. provisional Patent Application 60/580,108, entitled "METHOD AND APPARATUS FOR COLOR IMAGING A THREE-DIMENSIONAL STRUCTURE". These references are incorporated herein in their entirety by reference thereto.

In Step 130, the 3D virtual model W is manipulated to obtain digital representations of certain areas of interest in the oral cavity 10 for the design of the crown prosthesis, including the finish line 84, shoulder 85 and external surface 86 of the preparation 12.

Analysis of the 3D model W of the preparation in the intra oral cavity may be conducted, for example, by the dental lab 26, which typically comprises a laboratory, or a design or manufacturing entity that may provide direct technical services to the dental clinic in which the system 50 may be located. The location of the finish line 84 may be located using a suitable method and system, for example, as disclosed in U.S. patent application Ser. No. 10/623,707 and WO 04/008981, also assigned to the present assignee, and the contents of which are incorporated herein in their entirety. Alternatively, the finish line may be generated using methods disclosed in U.S. Pat. No. 5,266,030 the contents of which are incorporated herein. The virtual generation of the finish line may be incorporated as an integral component in the method of the invention.

Alternatively, the finish line 84 may be located in the 3D model W using any other means, including manual, automatic, interactive or any other means, or a combination of such means. Similar methods may be employed for defining the shoulder 85 (where appropriate, depending on the form of the finish line), and for defining the outer surface 86 of the preparation 12.

In step 140, the prosthesis geometry is designed. The prosthesis may comprise a single layer, or alternatively be multi-layered.

Figure 6:
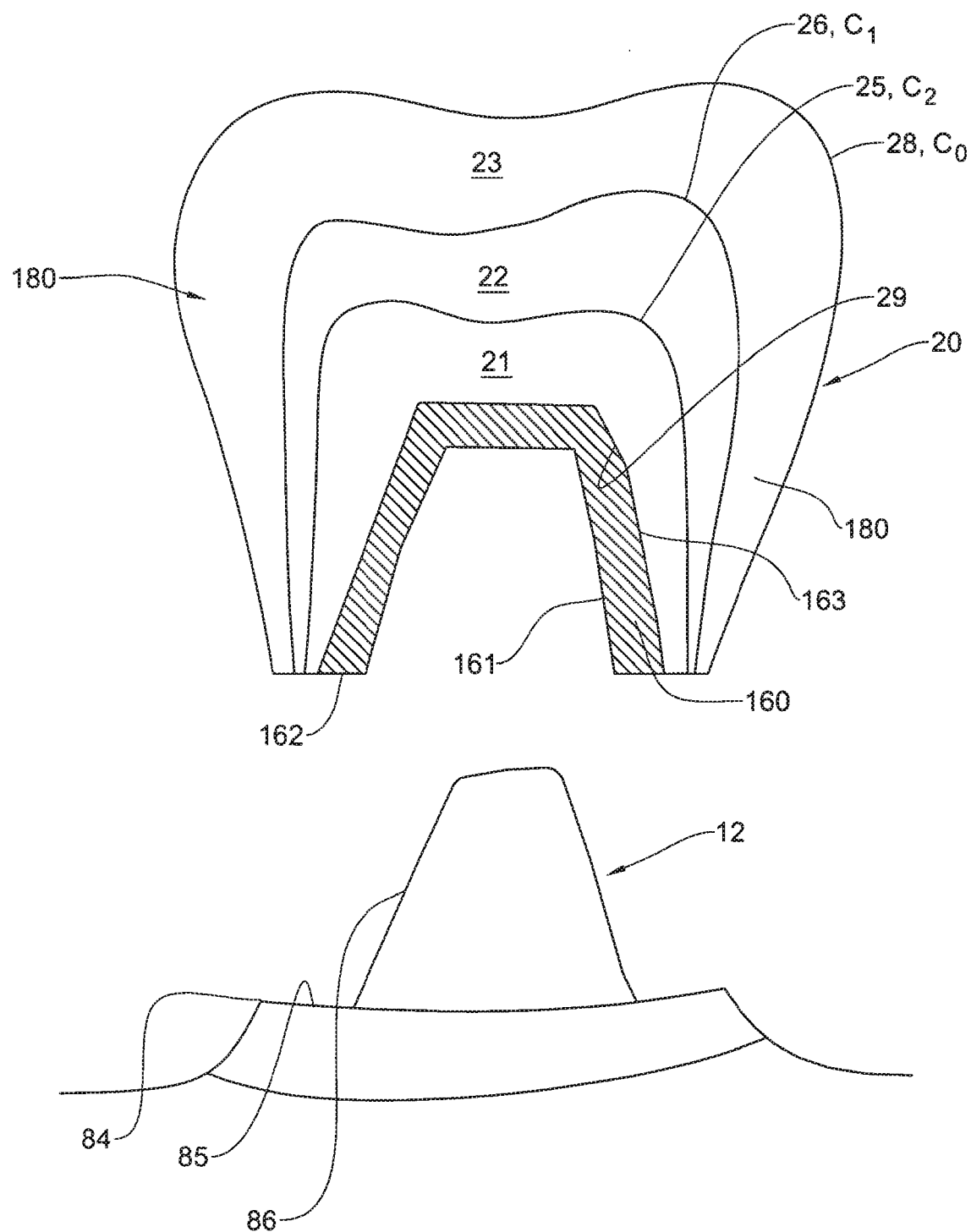
FIG. 6 illustrates a typical multi-layered 3D virtual model of a crown prosthesis.

Referring to FIG. 6, a virtual representation of such a crown, generally designated 20, is in the form of a cap 180 that is fitted onto a coping 160. The virtual coping 160 can be designed, and a real coping based on this design can be manufactured, using any suitable method. One such suitable manufacturing method is disclosed in copending applications U.S. patent application Ser. No. 10/814,653 and in PCT/IL2004/000290, entitled "METHOD AND SYSTEM FOR FABRICATING A DENTAL COPING, AND A COPING FABRICATED THEREBY", also assigned to the present Assignee. The contents of these references are incorporated herein in their entirety by reference thereto.

The coping 160 is typically made from a metal, ceramic or other very strong material, and is designed for taking the mechanical loads of the crown 20 associated with the normal activity of the teeth. The inner surface 161 and lower edge 162 of the coping 160 need to closely match the preparation 12 and finish line 84/shoulder 85, and moreover provide a reasonable insertion path for the crown 20. Typically, the fitting tolerance for the internal surface 161 and lower edge 162 needs to be in the order of about 40 microns or less, which is more demanding than for the cap 180. Typically, if the dimensional accuracy is not maintained to this tolerance level, there may be a risk of infection of the remaining parts of the tooth, the infection entering via the gap between the crown and the preparation, in particular between the lower edge 162 and the finish line 84. Furthermore, where such tolerances are not met, the life of the prosthesis may be severely reduced. Although prior art dental labs do design and manufacture copings, such close tolerances are not typically achievable by most regular dental labs that currently provide such services to clinics. Accordingly, the design and manufacture of the internal surface 161 and lower edge 162 may be advantageously carried out in the present invention by the service centre 23, which generally has the equipment to do so. By centralizing such specialized and accurate work from a number of clinics 22, the service center 23 is able to carry out such work in a more cost effective and efficient manner, and generally more accurately, than the dental lab 26.

Optionally, the processor 52 also has suitable software to define the inner surface 161 according to predetermined parameters. These parameters take into account the geometries of the external surface of the preparation 12 including finish line 84 and shoulder 85, the spacing required between the coping 160 and the preparation 12 to accommodate the adhesive or cement that is used to provide the bond between the two. The processor 52 may also comprise suitable software to provide the external shape of such a coping 160, and thus provide a complete geometrical representation or 3D data of the coping 160, digitally. The external surface 163 of the coping 160 may be defined in any number of ways. Typically, at least a majority of the external surface of the stump 82 is displaced from the internal surface thereof by a uniform amount to provide an approximately constant thickness throughout. However, the thickness of the coping 160 may vary for a number of reasons. For example, it may be necessary in some cases to provide a coping that is stronger in some parts than in others, reflecting the activity that the crown 20 will be expected to engage in—as a molar, incisor, canine and so on.

The cap 180, which may be formed from a single layer or from a plurality of partially or fully overlapping generally concentric layers, for example three layers 21, 22, 23, preferably has a natural looking appearance. Further, the dimensions of the crown 20, in particular the definition of the external surface 28 thereof depends on external factors and needs to be such as to enable the crown 20 to fit between the adjacent teeth A, B (FIG. 3). Of course, the number of layers and the extent of overlapping between each successive layer will generally vary from one prosthesis to another. Further, the external surface 28 is defined such as to provide adequate occlusion with the "working side" of the tooth and avoiding interfering contact between the crown 20 and teeth of the opposite jaw, in particular the opposing tooth D, when the crown is fixed onto the corresponding preparation 12 in the intraoral cavity 10.

An outer shape for the external surface 28 may be chosen in a number of ways. For example, if the original tooth that the crown 20 is replacing is still available, and the outer surface thereof is of a reasonable form, this original tooth may be scanned and the 3D data of the surface obtained. If necessary, this 3D data may be considered as a starting point, and the final shape of the external surface 28 is obtained by manipulating this data as required by the technician or other user that is designing the surface 28. Alternatively, if the patient has a reasonably healthy tooth on the same jaw but on the adjacent quadrant at a position corresponding to where the crown is to be fitted, the 3D data of the surface of this tooth is obtained. Optionally, this tooth may be scanned as described herein to obtain the 3D spatial coordinates thereof, unless this data may already be available from the 3D data of the oral cavity 10 stored in the processor 52. Typically, such 3D-data would need to be transformed to provide a lateral inversion of the coordinates, suitable for a prosthesis in the other half of the jaw. Alternatively, a suitable profile for surface 28 may be chosen and obtained from a library 35 (FIG. 5) that comprises the 3D spatial profiles of shapes or profiles of the outer surfaces of a plurality of crowns and teeth. If necessary the relative size and shape of the surface 28 may be adjusted by the user to better match the other teeth in the jaw. Then, the chosen surface is adjusted in any suitable manner, either manually, automatically, interactively or in any other manner, in order that the required target dimensions of surface 28 will fit within a control volume that defines the maximum dimensions of the crown 20, as required to conform to the space available in the intra oral cavity 10. In particular, the control volume may be chosen such as to provide adequate clearance between the crown and adjacent teeth, and adequate occlusion with the opposite teeth, when the crown 20 is properly fixed onto the preparation 12. A virtual representation $C_0$ of the external surface 28 is then defined.

In cases where the cap 180 comprises a number of layers, such as for example layers 21, 22, 23, the internal surface 29 of the virtual cap 180 is typically first defined, and the internal surface is substantially complementary to the external surface 163 of the coping 160. Accordingly, the 3D structure of the internal surface 29 may be obtained from the external surface 163, as described above, for example. Alternatively, if the real coping, that is, the physical coping, already exists, the external surface thereof can be directly scanned, for example in a similar manner to that described herein for the intraoral cavity, mutatis mutandis. If such an option is chosen, then the real coping may be scanned while fitted onto the preparation, and in fact Step 120 may be conducted with the coping in place on the preparation. Once the internal surface 29 and the external surface 28 are defined in virtual space, the characteristics of the internal layers 21, 22, 23 can be defined, taking into account the material from which the corresponding real, physical layers are to be made, according to any suitable rules and/or experience known to the user, to provide virtual 3D definitions $C_1$, $C_2$ of the external surfaces 25, 26, respectively, of internal layers 21, 22, respectively. The external surface of the outermost layer is the external surface 28 of the cap 180. The optical properties as well as the mechanical strengths of these materials are factors typically considered when designing the internal layers, as well as the shading desired for the crown 20. To assist in this process, shading data for the crown 20 may be obtained using the method disclosed in U.S. provisional Patent Application No. 60/580,109 entitled "METHOD FOR PROVIDING DATA ASSOCIATED WITH THE INTRAORAL CAVITY", also assigned to the present Assignee. The contents of this reference are incorporated herein in their entirety by reference thereto. Each of the internal layers 21, 22, and/or the external layer 23 may be full layers, covering completely the layer immediately below them including the coping, or may only partially cover inner layers and/or coping, for example comprising islands of material formed on the coping or an inner layer. Full flexibility as to the extent, thickness, and material of each layer is provided, enabling the strength of the prosthesis to be maximized while allowing the same to have a natural looking appearance that suitably matches other teeth of the intra oral cavity. In other embodiments, the crown 20 may be single-layered, and thus only the external surface 28 needs to be defined.

The design of the external surface 28, and where appropriate of the external surfaces 25, 26 (and optionally of the internal surface 161) may be executed by the processor 52 at the dental clinic, for example, or alternatively at the service center 23, or at the dental lab 26. If at the latter, and if use is made of a library of 3D spatial profiles of shapes or profiles of the outer surfaces of a plurality of crowns and teeth, and optionally also design rules for the internal layers, then the dental lab 26 can make use of library of the service centre 23, via communications network 24. Similarly, if the design is carried out at the dental clinic, the processor 52 may also make use of the library of the service centre 23, via communications network 24. Alternatively, the system 50 may have its own digital library 35 of 3D spatial profiles of shapes or profiles of the outer surfaces of a plurality of crowns and teeth, operatively connected to a processor 52 or other computer, as illustrated in FIG. 5, which comprises display 54 and user interface 59 such as a mouse and/or keyboard.

In Step 150, the processor 52 converts 3D data $C_0$, $C_1$, $C_2$ representative of the external surface 28 of the crown, and of the external surfaces 25, 26 respectively, into a set P of CNC instructions $P_0$, $P_1$, $P_2$ for machining the corresponding layers of wax, according to the method described in more detail below. Alternatively, the processor 52 sends the aforesaid 3D data to another processor 53, for example via network 24, that is particularly adapted for providing CNC instructions. In any case, the CNC instructions are then sent to a manufacturing center 60 directly or via network 24. Alternatively, the CNC instructions may be stored in any storage medium, for example magnetic tape, optical disk, and so on, and the medium physically sent to the manufacturing center 60 to be read and processed thereat.

Figure 7:
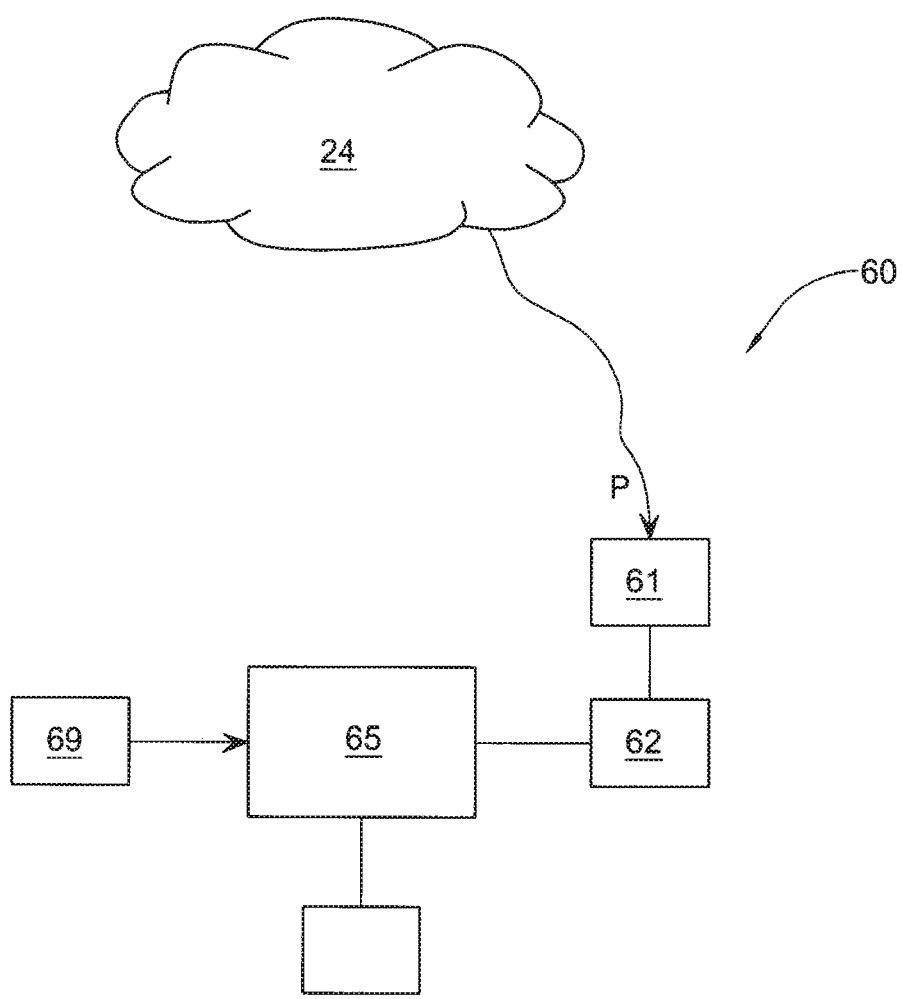
FIG. 7 schematically illustrates a system for manufacturing a dental prosthesis according to the invention.

Referring to FIG. 7, the manufacturing center 60 comprises an input facility 61 for receiving the set P of CNC data, for example via network 24 or via a physical storage medium, a processor 62, which processes the CNC data, and a machining center 65 that carries out a material removal operation on a workpiece based on CNC set of instructions P processed by the processor 62 to produce solid replicas in wax corresponding to the 3D data $C_0$, $C_1$, $C_2$.

Optionally, the manufacturing center 60, or indeed some other manufacturing center (not shown) may be adapted for producing a coping 160 directly from a suitable hard material, using the machining instructions, or indirectly via a lost wax process, for example as disclosed in the aforesaid applications entitled "METHOD AND SYSTEM FOR FABRICATING A DENTAL COPING, AND A COPING FABRICATED THEREBY". Alternatively, the coping 160 may be provided by means, indicated at 69, external to the manufacturing center 60.

The machining center 65 comprises any suitable machining tool that is adapted for material removal, and may include inter alia mechanical tools such as drills for example, laser tools such as for example laser drills or cutters, ultrasonic tools such as for example ultrasonic cutters, and so on. The machining paths and material removal characteristics of such tools can be finely controlled, typically by a control computer such as processor 62 comprised in or operatively connected to said machining center 65.

Operation of the manufacturing center 60, according to various implementations of the method of the invention, will now be described in greater detail with reference to FIG. 2.

In the first exemplary implementation of the method of the invention, and referring to FIGS. 2 and 8a to 8h, the method 200 is adapted for the fabrication of a multi-layered crown prosthesis 20. In this example, the prosthesis 20 comprises two internal layers over the coping, plus an outer layer, corresponding to layers 21, 22, 23 of the virtual model described above, but may be extended to prostheses having a greater number of full or partial layers in a similar manner to that described, mutatis mutandis. In step 210 of the method, a coping 160 is provided, substantially as described above.

Figure 8A:
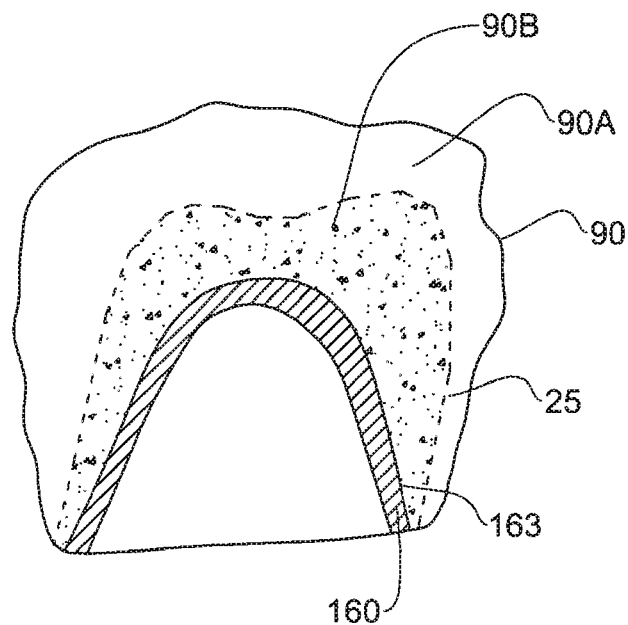
FIGS. 8a to 8h schematically illustrate various stages employed in the manufacture of a multi-layered crown prosthesis according to the invention.

Referring to FIG. 8a, in step 220, a wax layer 90 is applied to the external surface 163 of the coping. The wax layer 90 is sufficiently large so that it completely encloses the geometry defining the external surface 25 of the innermost virtual layer 21.

The set of wax models on the coping are made of relatively hard, durable wax or similar material. In particular, each wax model is made from a material that on the one hand lends itself to milling in a milling machine, while on the other hand has a low melting point and after melting, it has a kinematic viscosity sufficiently low to be usable in a lost wax technique known per se in the art of metal casting. Preferably, such a material has a melting point and congealing point of about 55° C. to about 80° C. and a kinematic viscosity of less than 90 m$^2$ sec. at about 100° C.

In Step 230 the machining center 65 then processes the CNC instructions $P_2$ corresponding to surface 25 (received at Step 150), applying a material removal operation to the wax layer 90 to remove all the wax 90A outside of the envelope represented by surface 25. Thus, a suitable milling or other machining process, for example, may be applied to the external surface of the wax layer. The remaining wax layer 90B after the material removal process is a physical wax model of layer 21 mounted on the coping 160.

Figure 8B:
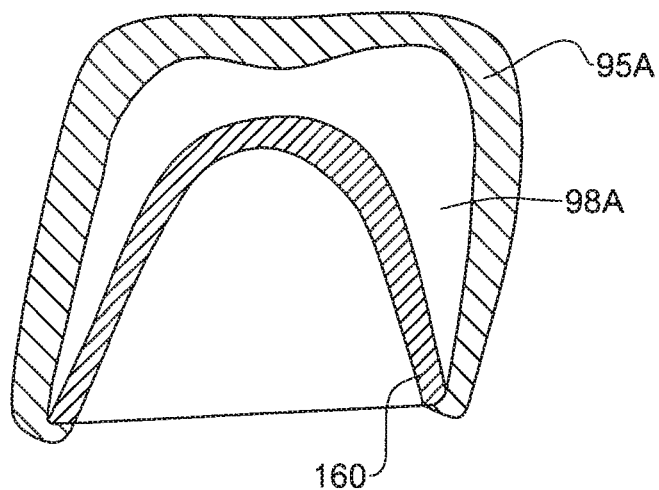
Figure 8C:
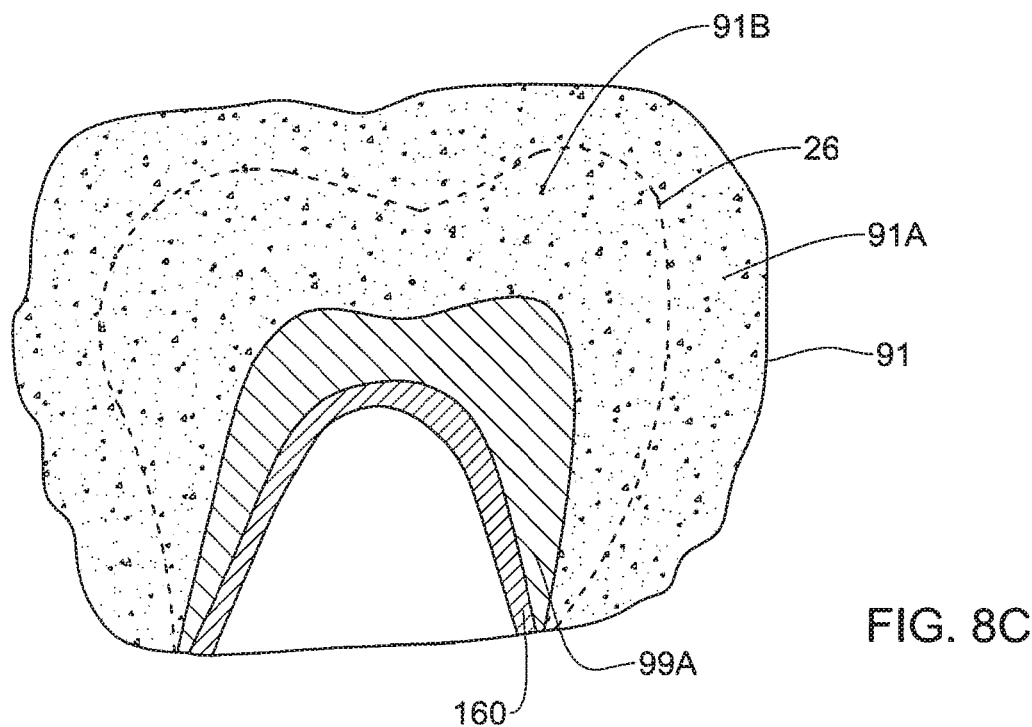
Figure 8D:
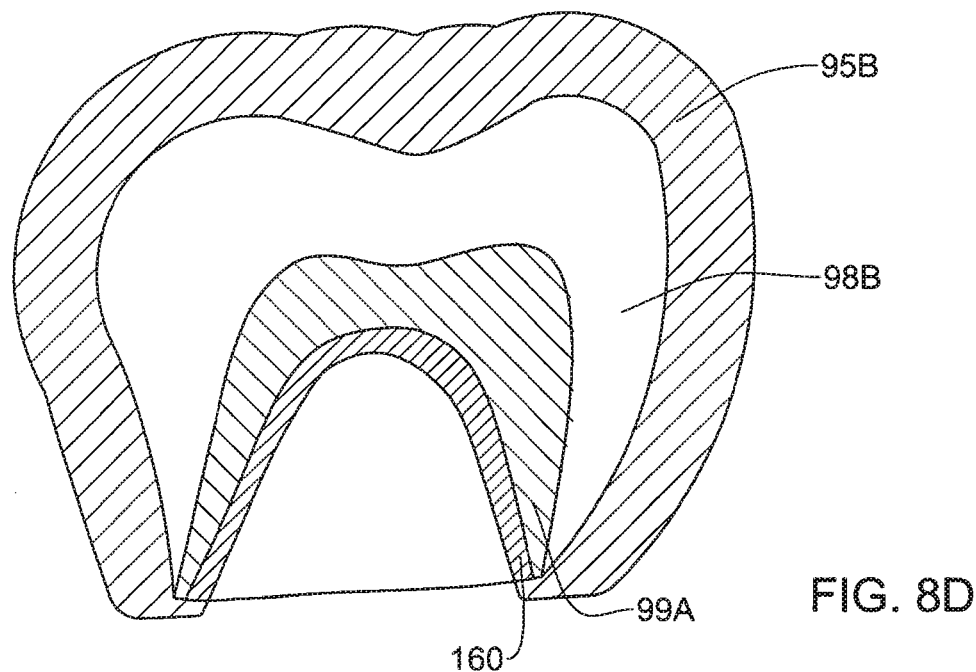

In Step 240, the wax layer 90B is invested in a material that solidifies onto the external side of the wax layer (still on the coping) and forms a mold 95A (FIG. 8b). Typically, access to the wax layer 90A is provided by means of a channel (not shown), for example.

Referring to FIG. 8b, and in Step 250, the combination provided in Step 240 is heated such that the wax layer 90B is burnt out, leaving a cavity 98A into which the innermost crown layer 99A may be cast. The burnt-out wax may be removed via the aforesaid channel, for example.

In Step 260—the innermost crown layer 99A is fabricated in the cavity 98A in any suitable way, for example by injecting a suitable molten metal into cavity 98A, and after hardening, the mold 95A is removed from the metal casting to provide a metal layer 99A.

Alternatively, such a lost wax process described with reference to Steps 240 to 260 may be based on a process used for the production of restorations as described by Ivoclar Vivadent Ltd. regarding the IPS Empress system in http://www.ivoclarco.uk/technician/nonmetal2.html, mutatis mutandis, for example. Essentially, the after the wax layer 90B is ready (mounted onto the coping), it is invested, and a leucite or lithium disilicate subframe, created through the IPS Empress system. These structures are then layered with leucite (for leucite sub-structure) or fluorapatite ceramic (over lithium disilicate framework) and then fired in the conventional ceramic furnace.

Alternatively, a suitable ceramic molding composition may be pressed into the cavity 98A, for example in a manner similar to that disclosed in U.S. Pat. No. 6,126,732, mutatis mutandis, the contents of which are incorporated herein in their entirety. Alternatively, sintering methods may be applied to the mold to produce a ceramic inner layer 99A. In each case, the mold 95A may have to be modified according to the details of the particular process used—for example, the mold may be divided into two or more parts that fit together to provide said cavity 98A.

In any case, a suitable method is used for providing a layer of crown material 99A based on the CNC machined layer of wax 90B.

Figure 8E:
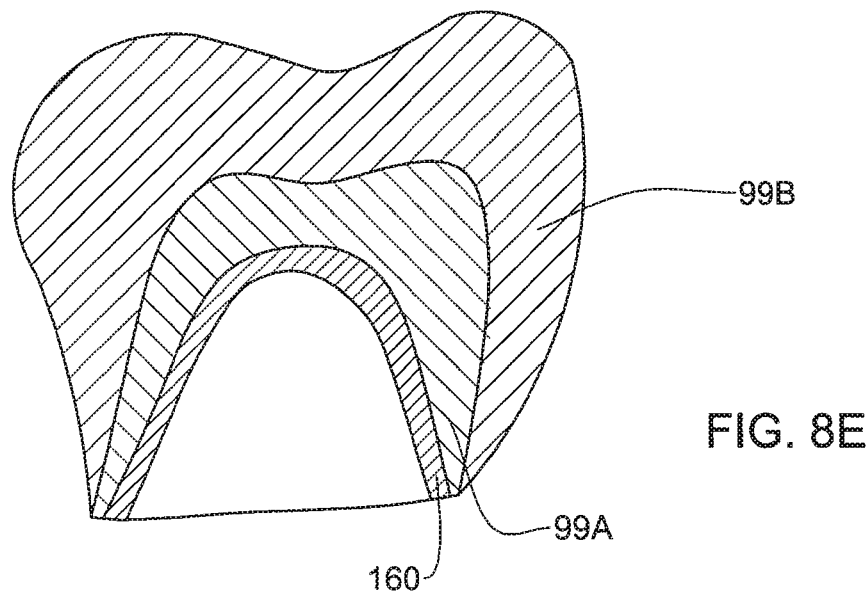

In Step 270, if this was the last layer required for the crown, Step 290 is implemented, otherwise, another layer is fabricated on the crown, continuing with Step 280. Since layer 99A is only the first of three layers for this particular example, the method of the invention according to this embodiment continues with step 280, and referring to FIG. 8c, a second wax layer 91 is applied, in a similar manner to that described above for Step 220 mutatis mutandis, but this time over the crown layer 99A rather than the coping 160. Of course, if the crown layer 99A only partially overlapped the coping, leaving parts of the coping exposed, then the new wax layer may, depending on the geometry of the second layer of the prosthesis, also overlap these exposed parts of the coping. Thus, the wax layer 91 is sufficiently large so that it completely encloses the geometry defining the external surface 26 of the next innermost virtual layer 22. Now, in Step 230, the machining center 65 then processes the CNC instructions P1 corresponding to surface 26 (received at Step 150), applying a material removal operation to the wax layer 91 to remove all the wax 91A outside of the envelope represented by surface 26. The remaining wax layer 91B is a physical wax model of layer 22 mounted on the coping previously fabricated crown layer 99A. In Step 240, the wax layer 91B is invested to form a mold 95B (FIG. 8d), and in Step 250, cavity 98B is formed into which the next crown layer 99B may be formed in Step 260, substantially as described for the first layer 99A, mutatis mutandis (FIG. 8e).

Figure 8F:
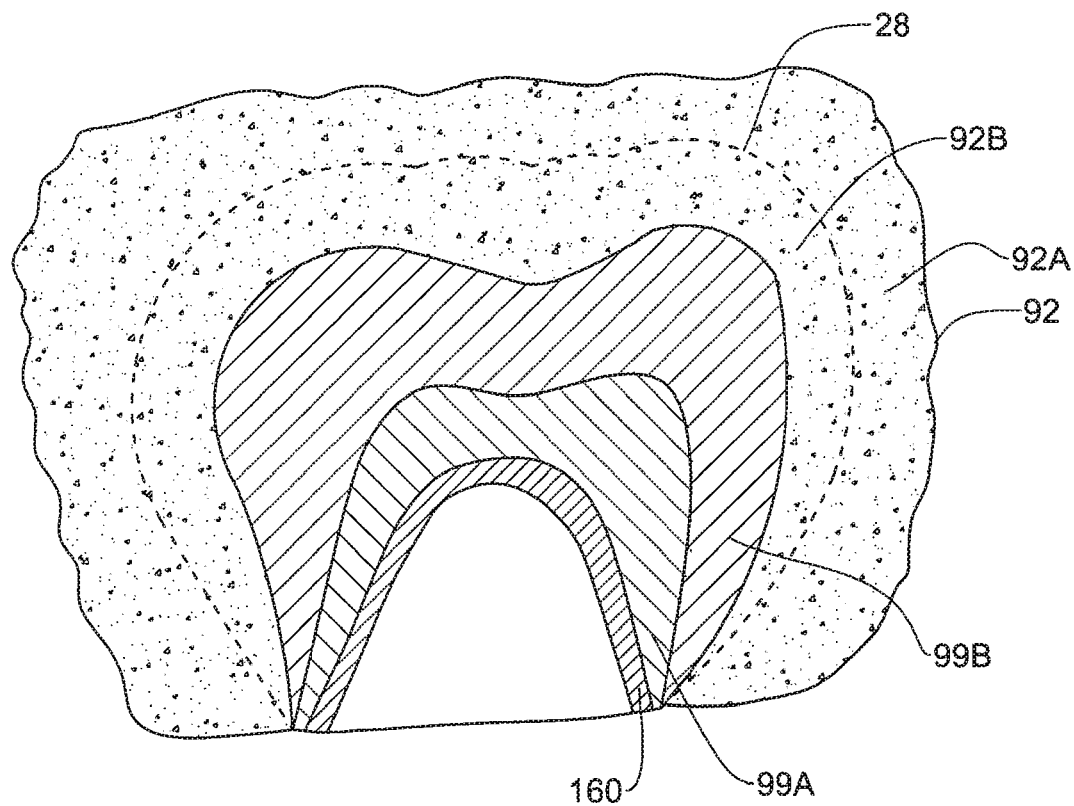
Figure 8G:
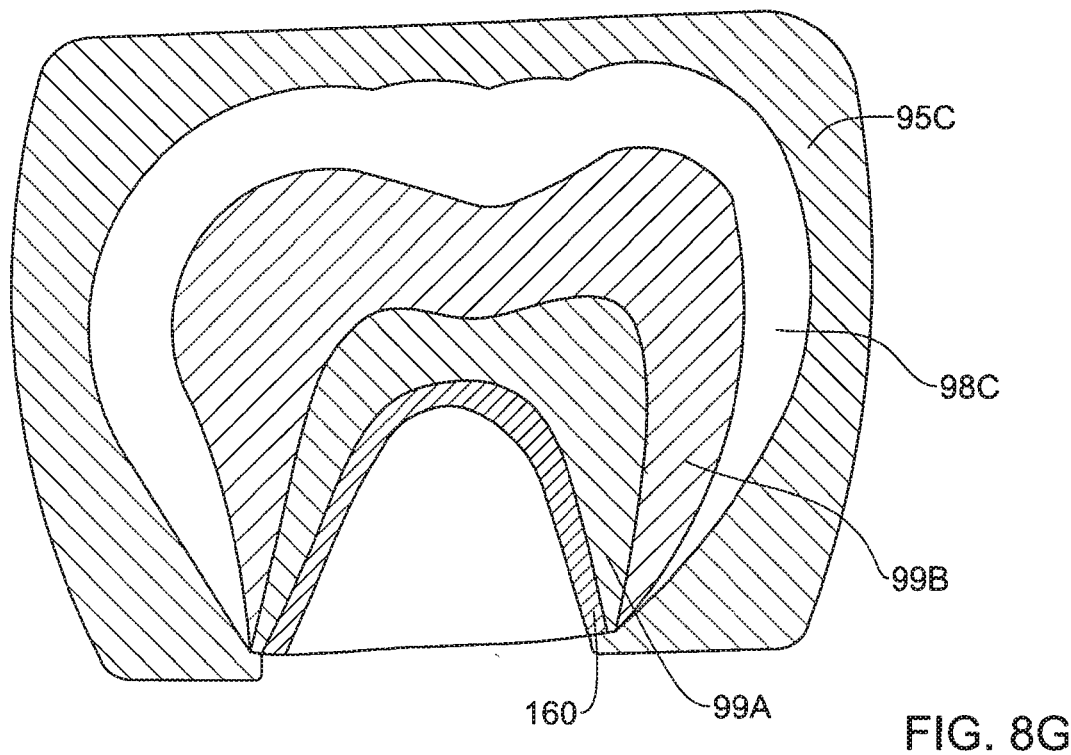
Figure 8H:
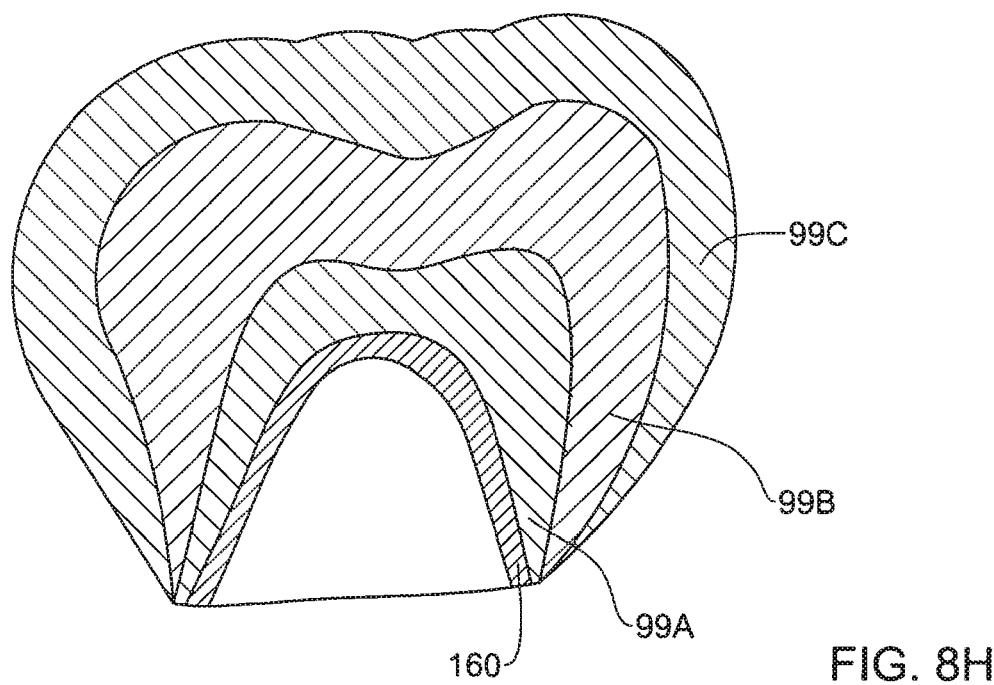

As there is still another layer to be added, Step 270 is followed by another cycle commencing at Step 280, wherein, referring to FIG. 8f, a third wax layer 92 is applied, in a similar manner to that described above for Step 220 mutatis mutandis, but this time over the second crown layer 99B rather than the first crown layer 99A or the coping 160. Of course, if the crown layer 99B only partially overlapped the first crown layer 99A and/or the coping, leaving parts of the crown layer 99A and/or coping exposed, then the new wax layer will, depending on the geometry of the second layer of the prosthesis, also overlap these exposed parts of the crown layer 99A and/or coping. Thus, the wax layer 92 is sufficiently large so that it completely encloses the geometry defining the external surface 28 of the crown. Now, in Step 230, the machining center 65 then processes the CNC instructions $P_O$ corresponding to surface 28 (received at Step 150), applying a material removal operation to the wax layer 92 to remove all the wax 92A outside of the envelope represented by surface 28. The remaining wax layer 92B is a physical wax model of layer 23 mounted on the previously fabricated crown layer 99B. In Step 240, the wax layer 92B is invested to form a mold 95C (FIG. 8g), and in Step 250, cavity 98C is formed into which the final crown layer 99C may be formed in Step 260, substantially as described for the first layer 99A or second layer 99B, mutatis mutandis (FIG. 8h).

At this stage, in Step 270 it is determined that this is the final layer fabricated according to the process of the invention, and the process ends at 290.

Alternatively, the final layer 99C of the crown may be built onto the previous layers 99B and 99A using manual (traditional) methods known per se in the art. In such a case, at the end of the second fabrication cycle, wherein the second layer 99B is completed, Step 270 is followed by Step 290, and then by a manual step (not shown) of preparing the final layer 99C.

In a second exemplary implementation of the method of the invention, and referring to FIGS. 2 and 9a to 9c, the method 200 is adapted for the fabrication of a single-layered crown prosthesis 20'. In this example, the prosthesis 20' comprises a single outer layer over the coping, corresponding to a combination of layers 21, 22, 23 of the virtual model described above, but without the interfacing surfaces 25, 26. In step 210 of the method, a coping 160 is provided, substantially as described above.

Figure 9A:
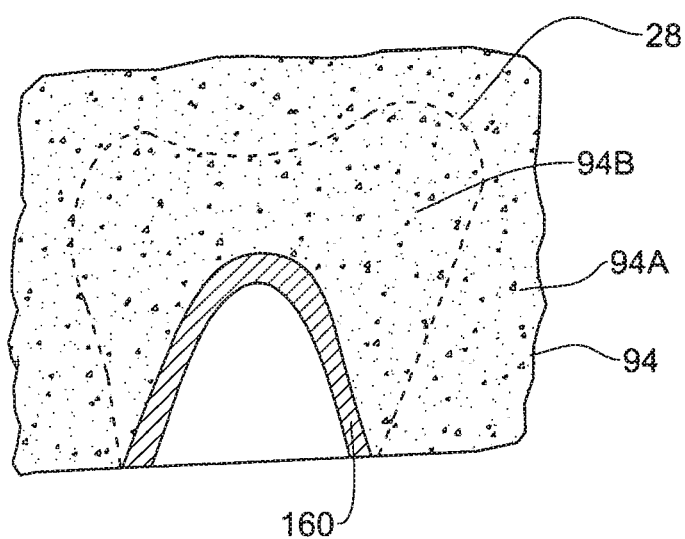
FIGS. 9a to 9c schematically illustrate various stages employed in the manufacture of a single-layered crown prosthesis according to the invention.
Figure 9B:
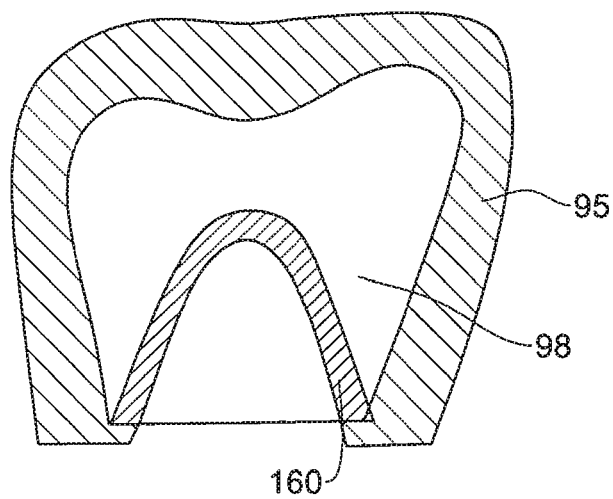
Figure 9C:
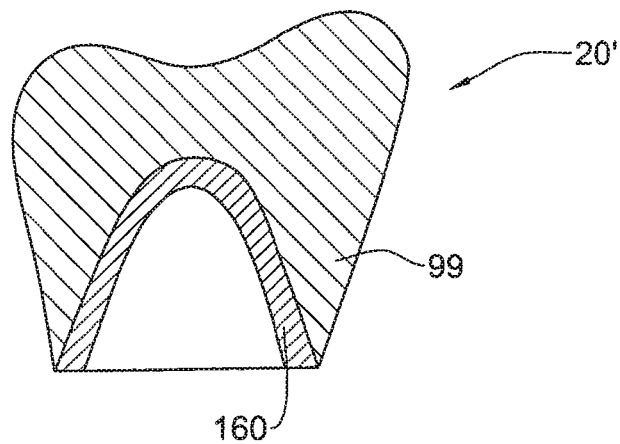

In Step 220 a wax layer 94 is applied onto the coping 160, sufficiently large so that it completely encloses the geometry defining the external surface 28. In Step 230, the machining center 65 then processes the CNC instructions $P_O$ corresponding to surface 28 (received at Step 150), applying a material removal operation to the wax layer 94 to remove all the wax 94A outside of the envelope represented by surface 28. The remaining wax layer 94B is a physical wax model of cap 180 mounted on the coping. In Step 240, the wax layer 94B is invested to form a mold 95 (FIG. 9b), and in Step 250, cavity 98 is formed into which the cap 180 in the form of crown layer 99 may be formed in Step 260, substantially as described for the first example above, mutatis mutandis (FIG. 9c). At this stage, in Step 270 it is determined that this is the final layer fabricated according to the process of the invention, and the process ends at 290.

In a third exemplary implementation of the method of the invention, and referring to FIGS. 2 and 10a to 10e, the method 200 is adapted for the fabrication of a double-layered bridge prosthesis 220. In this example, the prosthesis 220 comprises one internal layers over a pair of spaced copings, 212, 214, plus an outer layer, and these layers span two abutment teeth having a single pontic therebetween. Nevertheless, this application of the method may be extended to prostheses having a greater or lower number of layers, and to a greater number of pontics and/or connectors, for example in a similar manner to that described, mutatis mutandis.

The fabrication of the bridge prosthesis according to the invention is preceded by the definition of CNC material removing instructions for each layer of the prosthesis (Step 150), and typically this is accomplished in a similar manner to that described above for the crown prosthesis, mutatis mutandis. Thus, the intraoral cavity 10' is scanned to provide a 3D virtual model thereof, and this is manipulated and processed to provide a virtual model of the external surface of the prosthesis, a virtual model of the interface surface between the internal and external layer of the bridge (i.e., the external surface of the inner layer), CNC instructions corresponding to these two surfaces, and a pair of real copings 262, 264.

Thus, in step 210 of the method according to this embodiment, a pair of copings 262, 264 provided, each similar to the coping 160 substantially as described above, mutatis mutandis. The copings 262, 264 are adapted to fit onto preparations 212, 214, respectively, of the dental site (FIG. 4).

Figure 10A:
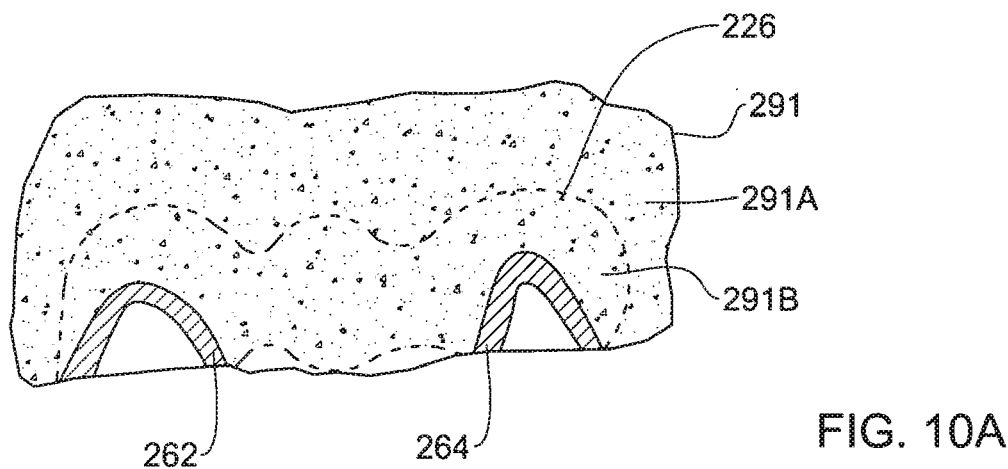
FIGS. 10a to 10e schematically illustrate various stages employed in the manufacture of a multi-layered bridge prosthesis according to the invention.
Figure 10B:
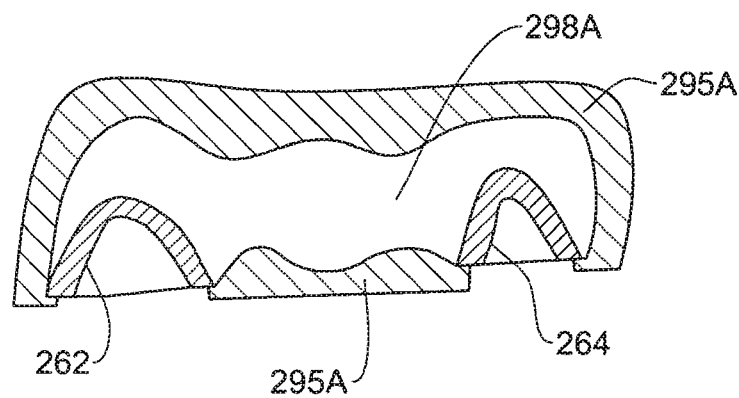
Figure 11:
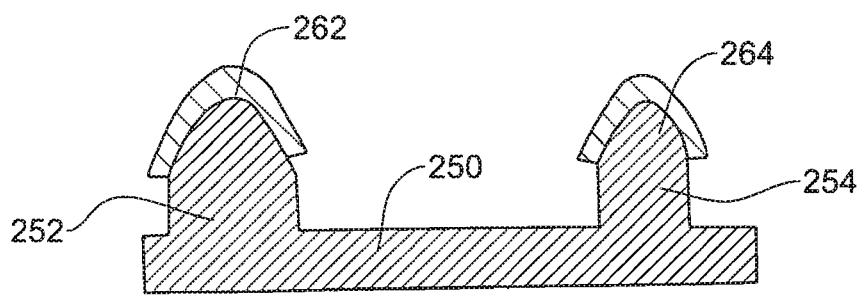
FIG. 11 illustrates a holder for maintaining the required spatial relationship between two copings used for manufacturing a bridge prosthesis

Referring to FIG. 10a, in Step 220 a wax layer 291 is applied onto the two copings 262, 264, this layer being sufficiently large so that it completely encloses the geometry defining the internal layer of the bridge 220. Advantageously, the spatial relationship between the two copings 262, 264, in relation to their mounting positions and orientations in the intraoral cavity 10' (FIG. 4), is maintained by temporarily mounting the copings onto a holder 250, illustrated in FIG. 11. The holder 250 comprises a pair of seats 252, 254 which comprise external surfaces substantially identical to the external surfaces of the preparations 212, 214, respectively, and moreover are spaced and oriented with respect to one another to mimic the spacing and orientation of the real preparations 212, 214 with respect to the intraoral cavity 10'. The holder 250, and in particular the seats 252 254 may be manufactured via a CNC machining operation based on the virtual model obtained in step 120 of the preprocess 100.

In Step 230, the machining center 65 then processes the CNC instructions corresponding to external surface 226 of the internal layer (received at Step 150), applying a material removal operation to the wax layer 291 to remove all the wax 291A outside of the envelope represented by surface 226. The remaining wax layer 291B is a physical wax model of internal layer mounted onto the two copings 262, 264. In Step 240, the wax layer 291B is invested to form a mold 295A (FIG. 10b), and in Step 250, cavity 298A is formed into which the bridge layer 299A may be formed in Step 260, substantially as described for the first example above, mutatis mutandis.

Figure 10C:
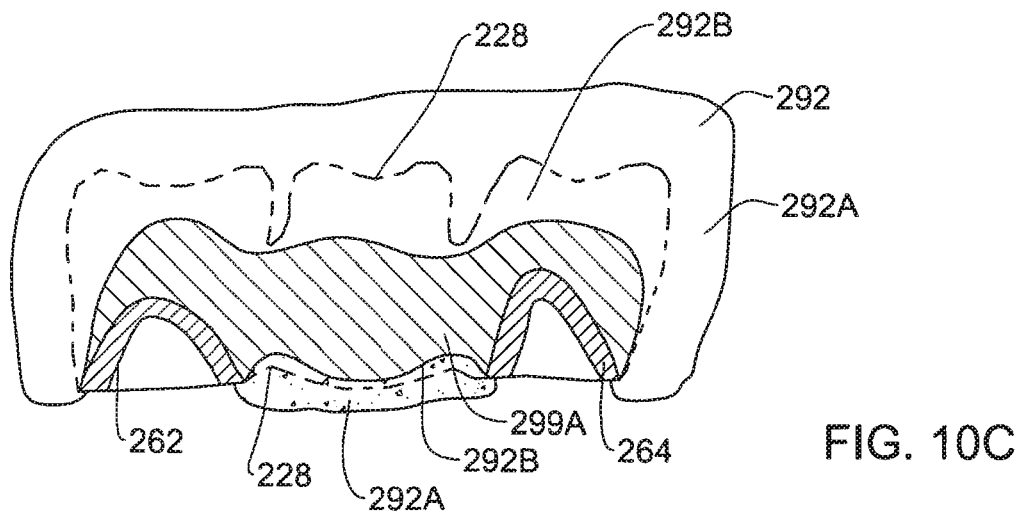
Figure 10D:
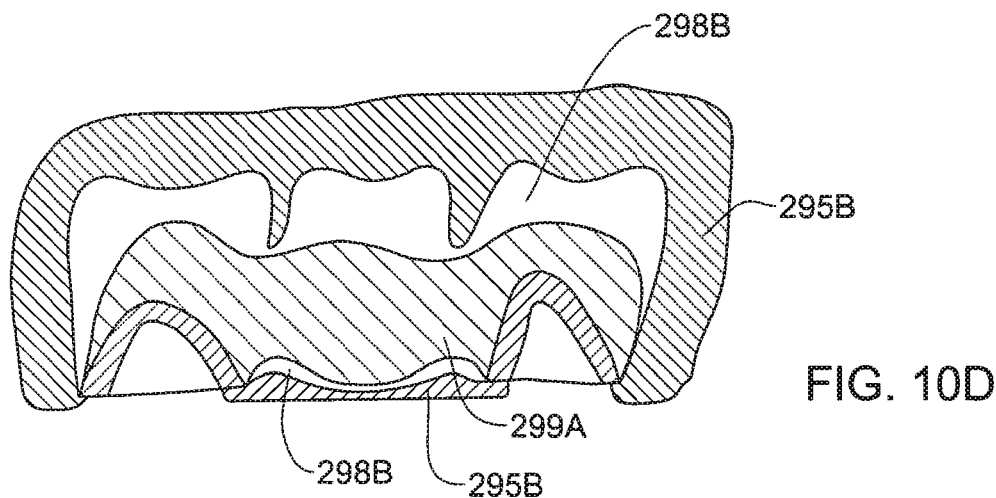
Figure 10E:
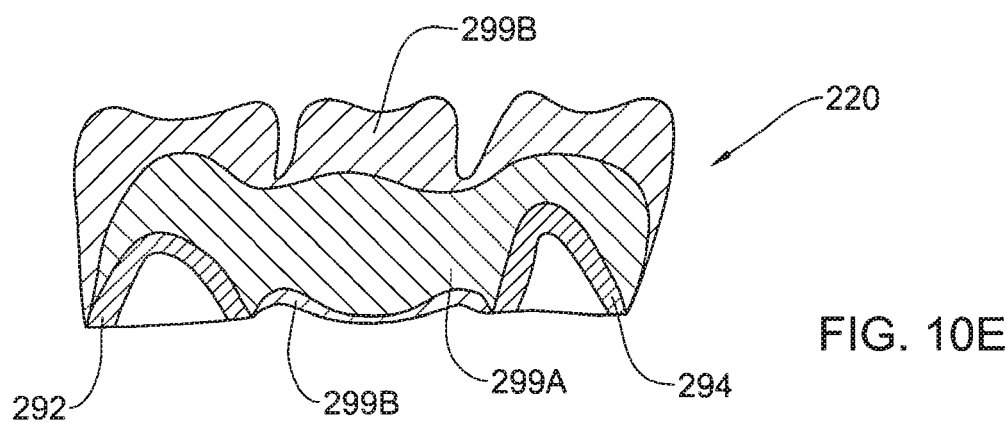

As there is still an outer layer to be added, to complete the prosthesis, Step 270 is followed by a second cycle commencing at Step 280, wherein, referring to FIG. 10c, a second wax layer 292 is applied, in a similar manner to that described above for Step 220 mutatis mutandis, but this time over the inner bridge layer 299A rather than the copings 262, 264. Thus, the wax layer 292 is sufficiently large so that it completely encloses the geometry defining the external surface 228 of the bridge. Now, in Step 230, the machining center 65 then processes the CNC instructions corresponding to surface 228 (received at Step 150), applying a material removal operation to the external wax layer 292, for example external machining (e.g. milling) of the wax layer, to remove all the wax 292A outside of the envelope represented by surface 228. The remaining wax layer 292B is a physical wax model of the final bridge layer mounted on the previously fabricated bridge layer 299A. In Step 240, the wax layer 292B is invested to form a mold 295B (FIG. 10d), and in Step 250, cavity 298B is formed into which the final bridge layer 29B may be formed in Step 260, substantially as described for the first layer 299A, mutatis mutandis (FIG. 10e).

At this stage, in Step 270 it is determined that this is the final layer fabricated according to the process of the invention, and the process ends at 290.

Alternatively, the final layer 299B of the bridge prosthesis may be built onto the previous layer 299A using manual (traditional) methods known per se in the art. In such a case, at the end of the first fabrication cycle, wherein the first layer 299A is completed, Step 270 is followed by Step 290, and then by a manual step (not shown) of preparing the final layer 299B.

Optionally, it is possible to join the copings 262, 264 via a connector, or indeed a pontic. This may be done after the copings are produced, or as part of the production process. For example, wax replicas of suitable connectors and/or one or more pontics are made, either manually or by any suitable method, including machining, casting and so on, and then the connectors and/or pontics are joined to the wax copings of the abutment teeth in a suitable manner, for example as is known in the art per se. The metal or ceramic structure for the bridge is then made from the wax model thereof in a similar manner to that disclosed in the aforesaid application entitled "METHOD AND SYSTEM FOR FABRICATING A DENTAL COPING, AND A COPING FABRICATED THEREBY". In any case, the connectors and/or pontics hold the two copings in their appropriate spatial relationships, and the method of the invention is then applied to the resulting structure in a similar manner to that described above for the bridge prosthesis, mutatis mutandis.

The invention is not bound by the specified example of FIGS. 8a to 11 and, accordingly, other scenarios may be used in addition or in lieu of the above, depending upon the particular application. Specifically, the invention can also be utilized in a less "digitized" scenario, for example one in which the care provider gathers the relevant information relating to the patient's dentition in a non-digitized manner (e.g. by taking a physical impression of the patient's dentition), and the patient's dentition data is digitized later on, at a laboratory.

Referring again to FIG. 5, the dental lab 26 is typically characterized as being equipped or otherwise able to design part or whole prostheses, and/or to partially manufacture or assemble the same, particularly where close tolerances are relatively less critical. On the other hand, while the service center 23 may also be equipped to design part or whole prostheses, and/or to fully or partially manufacture and/or assemble the same, it is particularly suited to do any of these activities where close or tight tolerances are in fact critical and/or difficult to achieve.

While the service centre 23 and dental labs 26 may be located in a different geographical zone to the dental clinic, for example, different countries, different cities in the same country, different neighborhoods in the same city, or even different buildings in the same neighborhood, they may also be housed in the same building, and in any case maintain their separate functions and capabilities, as described herein.

The system 50 may also be linked to one or more consultation centers 27, also via network 24, wherein such consultation centers 27 may comprise dental experts, for example, that may provide feedback to the user of system 50, based on data transmitted therefrom to the centers 27, according to the invention.

The invention allows to gather the 3D data that represents the patient's dentition in one place (say, the care provider's clinic), to design the virtual prosthesis model at the clinic or at a remote location, to generate the CNC set of instructions at another place and to fabricate the wax prosthesis at a yet another location. Furthermore, the invention allows for the fabrication of the wax layers and the prosthesis layers at different locations without damaging the quality of the prosthesis layers due to deformations in the wax models. It should be noted that additional, intermediate steps in which digital data is transmitted between remote locations might be carried-out as part of method of the invention.

The dental prosthesis manufactured according to the present invention is thus derived from a set of wax models, which due to the relatively softness of each model can be machined to a smoother surface texture than is possible when machining the prosthesis directly from the desired final material such as metal or a ceramic. Accordingly, dental prostheses produced using the method of the invention using the wax for preparing a mold are correspondingly smoother, and furthermore it is possible to include fine details in each layer, with respect to prostheses produced using direct material removal methods applied to the final material.

Furthermore, the wax-based method of the present invention for producing the dental prostheses has some advantages over direct material removal methods that are used elsewhere for producing the prostheses directly from the desired final material. For example less wear and breakage are experienced by the machining tool, and thus lowers costs. Furthermore, deformations of the tool, when a direct contact tool such as for example a mechanical tool is used, is less likely, and thus less deviations from the nominal dimensions of the coping with respect to the virtual model thereof occur than when producing a coping directly from a metal or other hard material.

In the method claims that follow, alphanumeric characters and Roman numerals used to designate claim steps are provided for convenience only and do not imply any particular order of performing the steps.

Finally, it should be noted that the word "comprising" as used throughout the appended claims is to be interpreted to mean "including but not limited to".

While there has been shown and disclosed exemplary embodiments in accordance with the invention, it will be appreciated that many changes may be made therein without departing from the spirit of the invention.

What is claimed is:

1. A method for producing a dental prosthesis on a dental coping, comprising:
   receiving a three-dimensional virtual model of the dental prosthesis;
   generating a plurality of virtual model layers based on the three-dimensional virtual model of the dental prosthesis;
   forming a plurality of wax layers corresponding to the plurality of virtual model layers; and
   casting a plurality of prosthesis layers from the plurality of wax layers, wherein at least one wax layer of the plurality of wax layers is formed on a previously cast prosthesis layer in order to form at least one prosthesis layer of the plurality of prosthesis layers on the previously cast prosthesis layer.

2. The method of claim 1, wherein each of the plurality of prosthesis layers corresponds to a respective wax layer of the plurality of wax layers, and wherein the at least one prosthesis layer on the previously cast prosthesis layer comprises an intermediate prosthesis layer corresponding to the at least one wax layer.

3. The method of claim 1, further comprising generating computerized numerical control (CNC) instructions, wherein the plurality of wax layers is formed by material removal operations based on the CNC instructions.

4. The method of claim 1, wherein the plurality of prosthesis layers is cast from the plurality of wax layers using a lost wax process.

5. The method of claim 1, wherein the dental prosthesis comprises a bridge or a crown.

6. The method of claim 1, wherein the three-dimensional virtual model comprises digital data representative of the surface topology of an intraoral cavity comprising a preparation.

7. The method of claim 1, wherein the plurality of prosthesis layers comprises one or more of a metal and a ceramic material.

8. The method of claim 1, further comprising generating the three-dimensional virtual model based on three-dimensional scan data of at least a portion of a patient's intraoral cavity where the dental prosthesis will be implanted.

9. A system for producing a dental prosthesis on a dental coping, comprising:
   one or more processors comprising instructions that, when executed, cause the system to,
      receive a three-dimensional virtual model of the dental prosthesis,
      generate a plurality of virtual model layers based on the three-dimensional virtual model of the dental prosthesis,
      produce the dental prosthesis on the coping based on the three-dimensional virtual model layers by forming a plurality of wax layers corresponding to the plurality of virtual model layers and casting a plurality of prosthesis layers from the plurality of wax layers, and
      form at least one wax layer of the plurality of wax layers on a previously cast prosthesis layer in order to cast at least one prosthesis layer of the plurality of prosthesis layers on the previously formed prosthesis layer.

10. The system of claim 9, wherein the one or more processors comprise instructions to fabricate the dental prosthesis with the plurality of prosthesis layers comprising an inner prosthesis layer having an internal surface shaped to fit an external surface of the dental coping, an outer prosthesis layer having an external surface corresponding to an external surface of the dental prosthesis, and at least one intermediate prosthesis layer between the inner and outer prosthesis layers.

11. The system of claim 10, wherein the one or more processors comprise instructions to form the inner prosthesis layer prior to forming the at least one intermediate prosthesis layer and form the at least one intermediate prosthesis layer prior to forming the outer prosthesis layer.

12. The system of claim 9, wherein the one or more processors further comprise instructions to,
   generate the three-dimensional virtual model, and
   generate fabrication instructions based on the three-dimensional virtual model.

13. The system of claim 12, wherein the one or more processors comprise instructions to generate the three-dimensional virtual model based on three-dimensional scan data of at least a portion of a patient's intraoral cavity where the dental prosthesis will be implanted.

14. The system of claim 12, wherein the instructions to generate the three-dimensional virtual model comprise instructions to,
   define an internal virtual model surface corresponding to an external surface of the dental coping,
   define an external virtual model surface corresponding to an external surface of the dental prosthesis, and
   define the plurality of virtual model layers between the internal virtual model surface and the external virtual model surface.

15. The system of claim 9, further comprising using an optical scanner to acquire the three-dimensional virtual model.

16. The system of claim 15, wherein the optical scanner comprises a probe for determining three dimensional structure by confocal focusing of an array of light beams.

17. A method for producing a dental prosthesis on a dental coping, comprising:

providing the dental coping;

forming a first wax layer on the dental coping based on a first virtual model layer of a three-dimensional virtual model of the dental prosthesis;

casting a first prosthesis layer from the first wax layer such that the first prosthesis layer is cast on the dental coping; and forming a second wax layer on the first prosthesis layer based on a second virtual model layer of the three-dimensional virtual model of the dental prosthesis.

18. The method of claim 17, wherein forming the first wax layer comprises:

applying wax on the dental coping so as to completely enclose a first surface corresponding to an outer surface of the first virtual model layer; and removing wax outside of the first surface.

19. The method of claim 18, wherein forming the second wax layer comprises:

applying wax on the first prosthesis layer so as to completely enclose a second surface corresponding to an outer surface of the second virtual model layer; and removing wax outside of the second surface.

\* \* \* \* \*